United States Patent
Elder, Jr. et al.

(10) Patent No.: US 10,729,674 B2
(45) Date of Patent: *Aug. 4, 2020

(54) NANOPARTICLE ISOFLAVONE COMPOSITIONS AND METHODS OF MAKING AND USING THE SAME

(71) Applicant: Humanetics Corporation, Edina, MN (US)

(72) Inventors: Edmund Joseph Elder, Jr., Madison, WI (US); Mark Joseph Sacchetti, Madison, WI (US); Randall Joseph Tlachac, Minneapolis, MN (US); John L. Zenk, Eden Prairie, MN (US)

(73) Assignee: Humanetics Corporation, Edina, MN (US)

( * ) Notice: Subject to any disclaimer, the term of this patent is extended or adjusted under 35 U.S.C. 154(b) by 89 days.

This patent is subject to a terminal disclaimer.

(21) Appl. No.: 16/026,546

(22) Filed: Jul. 3, 2018

(65) Prior Publication Data

US 2019/0160038 A1    May 30, 2019

Related U.S. Application Data

(60) Continuation of application No. 15/643,201, filed on Jul. 6, 2017, now Pat. No. 10,039,739, which is a continuation of application No. 15/258,866, filed on Sep. 7, 2016, now Pat. No. 9,724,325, which is a continuation of application No. 15/057,979, filed on
(Continued)

(51) Int. Cl.
| | |
|---|---|
| *A61K 9/14* | (2006.01) |
| *A61K 31/352* | (2006.01) |
| *A61K 9/00* | (2006.01) |
| *B82Y 5/00* | (2011.01) |

(Continued)

(52) U.S. Cl.
CPC .......... *A61K 31/352* (2013.01); *A61K 9/0019* (2013.01); *A61K 9/0053* (2013.01); *A61K 9/10* (2013.01); *A61K 9/14* (2013.01); *A61K 9/143* (2013.01); *A61K 9/145* (2013.01);
(Continued)

(58) Field of Classification Search
CPC ...... A61K 9/0019; A61K 9/0073; A61K 9/10; A61K 9/14; A61K 31/352; B82Y 5/00
See application file for complete search history.

(56) References Cited

U.S. PATENT DOCUMENTS

| | | |
|---|---|---|
| 4,390,559 A | 6/1983 | Zilliken |
| 5,302,401 A | 4/1994 | Liversidge et al. |

(Continued)

FOREIGN PATENT DOCUMENTS

| | | |
|---|---|---|
| EP | 2640188 | 9/2013 |
| JP | 2001309764 | 11/2001 |

(Continued)

OTHER PUBLICATIONS

Egberg, et al., Notice of Allowance dated Jan. 25, 2019 for U.S. Appl. No. 15/908,059.
(Continued)

*Primary Examiner* — Lakshmi S Channavajjala
(74) *Attorney, Agent, or Firm* — Stoel Rives LLP

(57) ABSTRACT

The present invention is directed to formulations of genistein and methods for making and using the same. In particular embodiments, the formulations described herein include suspension formulations of nanoparticulate genistein.

20 Claims, 7 Drawing Sheets

Related U.S. Application Data

Mar. 1, 2016, now Pat. No. 9,636,322, which is a continuation of application No. 14/524,936, filed on Oct. 27, 2014, now Pat. No. 9,308,167, which is a division of application No. 12/946,711, filed on Nov. 15, 2010, now Pat. No. 8,900,635.

(51) Int. Cl.
*B82Y 15/00* (2011.01)
*A61K 9/10* (2006.01)

(52) U.S. Cl.
CPC ............... *A61K 9/146* (2013.01); *B82Y 5/00* (2013.01); *B82Y 15/00* (2013.01)

(56) References Cited

U.S. PATENT DOCUMENTS

| | | | |
|---|---|---|---|
| 6,855,359 B2 | 2/2005 | Khare | |
| 7,655,694 B2 * | 2/2010 | Landauer | A61K 31/352 514/456 |
| 8,551,530 B2 | 10/2013 | Elder, Jr. et al. | |
| 8,900,635 B2 | 12/2014 | Elder et al. | |
| 9,084,726 B2 | 7/2015 | Egberg et al. | |
| 9,308,167 B2 | 4/2016 | Elder et al. | |
| 9,387,171 B2 | 7/2016 | Egberg et al. | |
| 9,636,322 B2 | 5/2017 | Elder et al. | |
| 9,724,325 B2 | 8/2017 | Elder et al. | |
| 9,782,384 B2 | 10/2017 | Egberg et al. | |
| 9,937,148 B2 | 4/2018 | Egberg et al. | |
| 10,039,739 B2 | 8/2018 | Elder et al. | |
| 2004/0164194 A1 | 8/2004 | Reed et al. | |
| 2004/0220116 A1 | 11/2004 | Behnam | |
| 2006/0116510 A1 | 6/2006 | Behnam | |
| 2006/0292214 A1 | 12/2006 | Jenkins et al. | |
| 2007/0020197 A1 | 1/2007 | Galli et al. | |
| 2007/0043121 A1 | 2/2007 | Brown et al. | |
| 2007/0087104 A1 | 4/2007 | Chanamai et al. | |
| 2007/0269526 A1 | 11/2007 | Bos et al. | |
| 2008/0311209 A1 * | 12/2008 | Beumer | A61K 8/498 424/489 |
| 2009/0035336 A1 * | 2/2009 | Vollhardt | A23L 33/105 424/401 |
| 2009/0035366 A1 | 2/2009 | Liversidge et al. | |
| 2011/0190399 A1 | 8/2011 | Kar et al. | |
| 2012/0121654 A1 | 5/2012 | Elder et al. | |
| 2012/0164190 A1 | 6/2012 | Elder et al. | |
| 2015/0050357 A1 | 2/2015 | Elder et al. | |
| 2016/0175276 A1 | 6/2016 | Elder et al. | |
| 2017/0304258 A1 | 10/2017 | Elder, Jr. et al. | |
| 2018/0000773 A1 | 1/2018 | Egberg et al. | |
| 2019/0038593 A1 | 2/2019 | Egberg et al. | |

FOREIGN PATENT DOCUMENTS

| | | |
|---|---|---|
| JP | 2004538242 | 12/2004 |
| JP | 2009067752 | 4/2009 |
| JP | 2013135655 | 7/2013 |
| JP | 6181733 | 7/2017 |
| JP | 2018008967 | 1/2018 |
| WO | 2006099165 | 9/2006 |
| WO | 2007000192 | 1/2007 |
| WO | 2007000193 | 1/2007 |
| WO | 2011091065 | 7/2011 |
| WO | 2011156774 | 12/2011 |
| WO | 2012068140 | 5/2012 |
| WO | 2015081018 | 6/2015 |

OTHER PUBLICATIONS

Egberg, et al., Notice of Allowance dated Mar. 24, 2017 for U.S. Appl. No. 15/172,665.
Elder, et al., Office Action dated Mar. 21, 2012 for U.S. Appl. No. 12/946,711.
Elder, et al., Office Action dated Mar. 28, 2012 for U.S. Appl. No. 13/411,405.
Elder, et al., Office Action dated Nov. 21, 2016 for U.S. Appl. No. 15/057,979.
Elder, et al., Office Action dated Oct. 11, 2016 for U.S. Appl. No. 15/258,866.
Elder, et al., Office Action dated Oct. 8, 2013 for U.S. Appl. No. 12/946,711.
Elder, et al., Office Action dated Sep. 11, 2012 for U.S. Appl. No. 13/411,405.
Elder, et al., Office Action dated Sep. 11, 2017 for U.S. Appl. No. 15/643,201.
Elder, et al., Preliminary Amendment filed Oct. 27, 2014 for U.S. Appl. No. 14/524,936.
Elder, et al., Response to Office Action dated May 22, 2013 for U.S. Appl. No. 13/411,405.
Elder, et al., Response to Office Action filed Aug. 1, 2016 for U.S. Appl. No. 15/057,979.
Elder, et al., Response to Office Action filed Aug. 12, 2015 for U.S. Appl. No. 14/524,936.
Elder, et al., Response to Office Action filed Dec. 11, 2012 for U.S. Appl. No. 13/411,405.
Elder, et al., Response to Office Action filed Dec. 5, 2017 for U.S. Appl. No. 15/643,201.
Elder, et al., Response to Office Action filed Feb. 14, 2013 for U.S. Appl. No. 12/946,711.
Elder, et al., Response to Office Action filed Feb. 7, 2017 for U.S. Appl. No. 15/258,866.
Elder, et al., Response to Office Action filed Jun. 21, 2012 for U.S. Appl. No. 12/946,711.
Elder, et al., Response to Office Action filed Jun. 27, 2012 for U.S. Appl. No. 13/411,405.
Elder, et al., Response to Office Action filed Mar. 7, 2014 for U.S. Appl. No. 12/946,711.
Fitzpatrick, et al., Soy Isoflavones: Hope or Hype?, Mar. 14, 2003; 44 Supl 1: S21-9.
Goodman-Gruen, et al., Usual Dietary Isoflavone Intake and Body Composition in Postmenopausal Women, Menopause. Sep.-Oct. 2003; 10(5): 427-32.
Landauer, et al., Genistein Treatment Protects Mice from Ionizing Radiation Injury, J. Appl. Toxicol. (2003) 23: 379-385.
Landauer, et al., Prevention of Gamma Radiation-Induced Mortality in Mice by the Isoflavone Genistein, Human Factors and Medicine Panel Research Task Group meeting Bethesda, Maryland Jun. 21-23, 2005.
Landauer, et al., Radioactive and Locomotor Responses of Mice Treated with Nimodipine Alone and in Combination with WR-151327, J. App. Toxicol. (2001) 21:25-31.
Leonarduzzi, et al., Design and Development of Nanovehicle-Based Delivery Systems for Preventative or Therapeutic Supplementation with Flavonoids, Curr Med Chem. 2010; 17(1): 74-95.
Magee, et al., Phyto-Oestrogens, Their Mechanism of Action: Current Evidence for a Role in Breast and Prostate Cancer, Br J Nutr. Apr. 2004; 91(4): 513-31.
Messina, et al., Emerging Evidence on the Role of Soy in Reducing Prostate Cancer Risk, Nutr Re. Apr. 2003; 61(4): 117-31.
Mohammad, et al., Genistein Sensitizes Diffuse Large Cell Lymphoma to CHOP (cyclophosphamide, doxorubicin, vincristine, prednisone) Chemotherapy, Mol Cancer Ther. Dec. 2003; 2(12): 1361-8.
Morabito, et al., Effects of Genistein and Hormone-Replacement Therapy on Bone Loss in Early Postmenopausal Women: A Randomized Double-Blind Placebo-Controlled Study, J Bone Miner Res. Oct. 2002; 17(10); 1904-12.
Nicosia, et al., Oncogenic Pathways Implicated in Ovarian Epithelial Cancer, Hematol Oncol Clin North Am. Aug. 2003; 17(4): 927-43.
Park, et al., Chemopreventive Potential of Epigallocatechin Gallate and Genistein: Evidence from Epidemiological and Laboratory Studies, Toxicol Lett. Apr. 15, 2004; 150(1): 43-56.
Roomans, et al., Pharmacological Approaches to Correcting the Ion Transport Defect in Cystic Fibrosis, Am J Respir Med. 2003; 2(5): 413-31.

(56) References Cited

OTHER PUBLICATIONS

Sarkar, et al., Lesson Learned from Nature for the Development of Novel Anti-Cancer Agents: Implication of Isoflavone, Curcumin, and Their Synthetic Analogs, Curr Pharm Des. Jun. 2010; 10(16): 1801-12.
Sarkar, et al., Soy Isoflavones and Cancer Prevention, Cancer Invest. 2003; 21(5): 744-57.
Setchell, et al., Dietary Phytoestrogens and Their Effect on Bone: Evidence From in Vitro and In Vivo, Human Observational, and Dietary Intervention Studeies 1-3, Am J. Clin Nutr. Sep. 2003; 78(3 Suppl); 593S-609S.
Si, et al., Improving the Anti-Tumor Effect of Genistein with a Biocompatible Superparamagnetic Drug Delivery System, J Nanosci Nanotechol. Apr. 2010; 10(4):2325-31.
Singh, et al., Singh, et al., "Effects of genistein administration on cytokine induction in whole-body gamma," International Immunopharmacology, vol. 9, pp. 1401-1410, (2009).
Singh, et al., Effects of Genistein Administration on Cytokine Induction in Whole-Body Gamma, International Immunopharmacology, vol. 9, pp. 1401-1410, (2009).
Sun, et al., Pilot Study of Specific Dietary Supplement in Tumor-Bearing Mice and in Stage IIIB and IV Non-Small Cell Lung Cancer Patients, Nutr Cancer. 2001; 39(1): 85-95.
Takahashi, et al., How to Make and Use Nanoparticulate Isoflavone Composition, and Manufacturing Thereof, Recent Progress in Physiochemical Characterization and Formulation Technologies for Poorly Soluble Drugs, Jan. 2010, first edition, pp. 146-150.
Takimoto, et al., Phase I Pharmacokinetic and Pharmacodynamic Analysis of Unconjugated Soy Isoflavones Adminstered to Individuals with Cancer, Cancer Epidemiol Biomarkers Prev. Nov. 2003; 12(11Pt1): 1213-21.
Urban, et al., Urban, et al., "The Effect of Isolated Soy Protein on Plasma Biomarkers in Elderly Men with Elevated Serum Prostate Specific Antigen." J Urol. Jan. 2001; 165(1): 294-300.
Urban, et al., The Effect of Isolated Soy Protein on Plasma Biomarkers in elderly Men with Elevated Serum Prostate Specific Antigen, J Urol. Jan. 2001; 165(1): 294-300.
Wei, et al., Isoflavone Genistein: Photoprotection and Clinical Implications in Dermatology, J. Nutr. Nov. 2003; 133(11 Suppl 1): 3811S-3819S.
Young, et al., Why are Low-Density Lipoproteins Atherogenic, WJM, vol. 160, No. 2, pp. 153-164, Feb. 1994.
Zhou, et al., Genistein Stimulates Hematopoiesis and Increases Survival in Irradiated Mice, J. Radiat. Res., 46(4) 425-433 (2003).
Amendment and Response to Final Office Action dated Dec. 1, 2016 for U.S. Appl. No. 15/057,979.
Corrected Notice of Allowance dated Apr. 9, 2018 for U.S. Appl. No. 15/643,201.
European Examination Report dated Aug. 24, 2017 for EP application No. 11840762.6.
European Search Report dated Mar. 21, 2014 for EP application 11840762.6.
European Search Report dated Mar. 28, 2017 for EP application 14865904.8.
International Preliminary Report on Patentability (IPRP) dated May 21, 2013 for international application PCT/US2011/060829.
International Search Report and Written Opinion dated Mar. 23, 2012 in International Application PCT/US2011/060829.
Notice of Allowance dated Apr. 3, 2018 for U.S. Appl. No. 15/643,201.
Office Action as received for Canadian Patent Application No. 2,852,410 dated Oct. 30, 2017.
Office Action dated May 23, 2018 for Israel Application No. 226377.
Response to Office Action dated Apr. 18, 2018 for Canada Application No. 2,852,410.
Response to the Examination Report dated Mar. 2, 2018 for EP Application No. 11840762.6.
International Search Report and Written Opinion dated Feb. 6, 2015 for international application PCT/US2014/067141 ,9.

Atkinson, et al., The Effects of Phytoestrogen Isoflavones on Bone Density in Women: a Double-Blind, Randomized, Pacebo-Controlled Trial 1-3, Am J. Clin Nutr. Feb. 2004: 79(2): 326-33.
Bhathena, et al., Beneficial Role of Dietary Phytoestrogens in Obesity and Diabetes1,2, Am J Clin Nutr. Dec. 2002; 76(6): 1191-201.
Chait, et al., Low Density Lipoprotein Oxidation and the Pathogenesis of Atherosclerosis, WLM, vol. 160, No. 2, pp. 183-184. Feb. 1994.
Cliffton-Bligh, et al., The Effect of Isoflavones Extracted From Red Clover (Rimostil) on Lipid and Bone Metabolism, Menopause. Jul.-Aug. 2001; 8(4): 259-65.
Cotter, et al., Genistein Appears to Prevent Early Postmenopausal Bone Loss as Effective as Hormone Replacement Therapy, Nutr Rev. Oct. 2003; 61(10): 346-51.
Egberg, et al., Notice of Allowance dated Jun. 2, 2017 for U.S. Appl. No. 15/172,665.
Egberg, et al., Notice of Allowance dated Mar. 14, 2016 for U.S. Appl. No. 14/740,018.
Egberg, et al., Notice of Allowance dated Mar. 24, 2015 for U.S. Appl. No. 14/090,864.
Egberg, et al., Notice of Allowance dated Nov. 30, 2017 for U.S. Appl. No. 15/694,542.
Egberg, et al., Office Action dated Apr. 23, 2014 for U.S. Appl. No. 14/090,864.
Egberg, et al., Office Action dated Jan. 13, 2017 for U.S. Appl. No. 15/172,665.
Egberg, et al., Office Action dated Jan. 14, 2016 for U.S. Appl. No. 14/740,018.
Egberg, et al., Office Action dated Jul. 31, 2014 for U.S. Appl. No. 14/090,864.
Egberg, et al., Office Action dated Nov. 6, 2014 for U.S. Appl. No. 14/090,864.
Egberg, et al., Preliminary Amendment filed Jun. 15, 2015 for U.S. Appl. No. 14/7450,018.
Egberg, et al., Preliminary Amendment filed Nov. 26, 2013 for U.S. Appl. No. 14/090,864.
Egberg, et al., Preliminary Amendment filed Sep. 25, 2017 for U.S. Appl. No. 15/694,542.
Egberg, et al., Response to Office Action filed Feb. 16, 2017 for U.S. Appl. No. 15/172,665.
Egberg, et al., Response to Office Action filed Feb. 24, 2016 for U.S. Appl. No. 14/7450,018.
Egberg, et al., Response to Office Action filed Feb. 4, 2015 for U.S. Appl. No. 14/090,864.
Egberg, et al., Response to Office Action filed Jul. 10, 2014 for U.S. Appl. No. 14/090,864.
Egberg, et al., Response to Office Action filed Sep. 24, 2014 for U.S. Appl. No. 14/090,864.
Elder, et al., Corrected Notice of Allowability dated Sep. 18, 2014 for U.S. Appl. No. 12/946,711.
Elder, et al., Corrected Notice of Allowability dated Sep. 9, 2014 for U.S. Appl. No. 12/946,711.
Elder, et al., Interview Summary dated Dec. 14, 2012 for U.S. Appl. No. 12/946,711.
Elder, et al., Interview Summary dated Dec. 14, 2012 for U.S. Appl. No. 13/411,405.
Elder, et al., Interview Summary dated May 29, 2013 for U.S. Appl. No. 13/411,405.
Elder, et al., Notice of Allowance dated Apr. 10, 2017 for U.S. Appl. No. 15/258,866.
Elder, et al., Notice of Allowance dated Dec. 4, 2015 for U.S. Appl. No. 14/524,936.
Elder, et al., Notice of Allowance dated Jan. 3, 2017 for U.S. Appl. No. 15/057,979.
Elder, et al., Notice of Allowance dated Jul. 30, 2014 for U.S. Appl. No. 12/946,711.
Elder, et al., Notice of Allowance dated Jun. 24, 2013 for U.S. Appl. No. 13/411,405.
Elder, et al., Office Action dated Apr. 16, 2015 for U.S. Appl. No. 14/524,936.
Elder, et al., Office Action dated Apr. 4, 2016 for U.S. Appl. No. 15/057,979.

(56) References Cited

OTHER PUBLICATIONS

Elder, et al., Office Action dated Aug. 31, 2012 for U.S. Appl. No. 12/946,711.
Elder, et al., Office Action dated Feb. 22, 2013 for U.S. Appl. No. 13/411,405.

* cited by examiner

NANOPARTICLE ISOFLAVONE COMPOSITIONS AND METHODS OF MAKING AND USING THE SAME

RELATED APPLICATION DATA

This application is a continuation of U.S. patent application Ser. No. 15/643,201, filed Jul. 6, 2017, which issued as U.S. Pat. No. 10,039,739 on Aug. 7, 2018, which is a continuation of U.S. patent application Ser. No. 15/258,866, filed Sep. 7, 2016, which issued as U.S. Pat. No. 9,724,325 on Aug. 8, 2017, which is a continuation of U.S. patent application Ser. No. 15/057,979, filed Mar. 1, 2016, which issued as U.S. Pat. No. 9,636,322 on May 2, 2017, which is a continuation of U.S. patent application Ser. No. 14/524,936, filed Oct. 27, 2014, which issued as U.S. Pat. No. 9,308,167 on Apr. 12, 2016, which is a divisional of U.S. patent application Ser. No. 12/946,711, filed Nov. 15, 2010, which issued as U.S. Pat. No. 8,900,635 on Dec. 2, 2014; the entire contents of each of the foregoing applications are hereby incorporated by reference herein.

TECHNICAL FIELD

The present invention relates to compositions including genistein and methods for producing and utilizing such compositions.

BACKGROUND

Genistein is a pharmaceutically active isoflavone. In the body, genistein interacts with various enzymes that have wide-ranging actions in many tissues. Therefore, the potential therapeutic impacts of genistein are diverse. However, genistein has proven difficult to formulate and deliver to subjects in a manner that achieves and maintains therapeutically effective blood plasma levels.

DETAILED DESCRIPTION OF PREFERRED EMBODIMENTS

Figure 1:
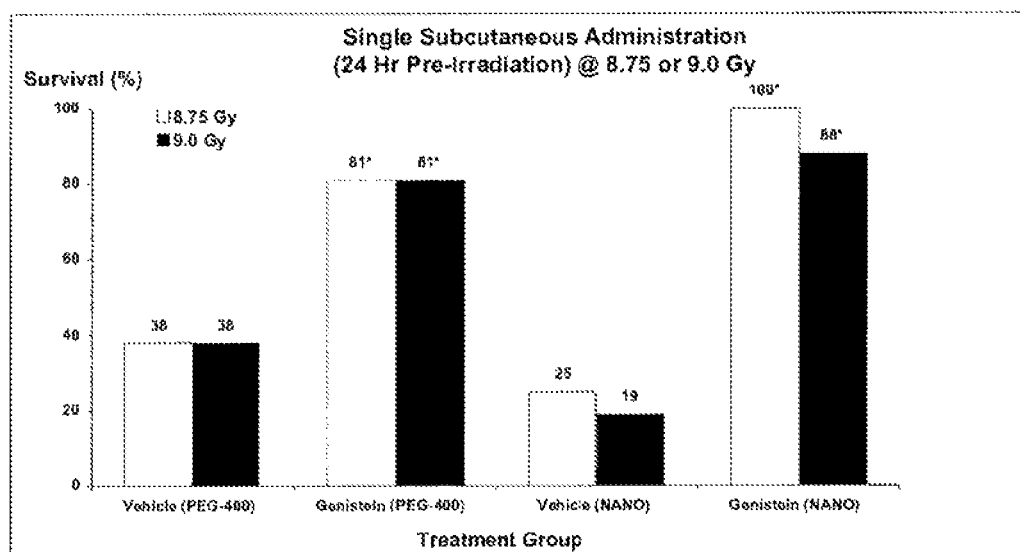
FIG. 1 shows the thirty-day survival rates in groups of mice receiving a solution formulation of genistein versus the thirty-day survival rates in groups of mice receiving a genistein suspension formulation as described herein.

Compositions of genistein compounds are described herein. In particular embodiments, the compositions described herein are pharmaceutical formulations suitable for oral or parenteral administration. Generally, given the desired therapeutic applications for genistein, it is desirable to deliver genistein to a subject in a manner that (i) achieves a therapeutic blood plasma concentration in a relatively short period of time and (ii) maintains a therapeutic blood plasma concentration over an extended period of time. Using available formulations of genistein, however, it has been found that relatively high doses of genistein are often required to achieve and maintain therapeutic blood plasma concentrations of genistein. This is particularly true when genistein is administered orally. However, even when genistein is formulated for parenteral administration (e.g., via intravenous injection or infusion, intravascular injection, subcutaneous injection, or intramuscular injection), it is often the case that relatively large volumes of drug formulation must be delivered in order to achieve and maintain therapeutic blood plasma concentrations.

Genistein is practically insoluble in water, requiring greater than 50,000 parts water at 25° C. to dissolve one part genistein. Furthermore, when delivered orally, genistein has shown poor bioavailability, which may be due, at least in part, to the compound's low water solubility. Therefore, in light of genistein's generally low bioavailability and water solubility, achieving and maintaining therapeutic blood plasma concentrations of genistein can require high doses of genistein delivered at relatively high dose frequencies. Genistein compositions with high concentrations of genistein that provide significantly increased bioavailability are described herein. Moreover, in particular embodiments, the genistein compositions described herein maintain therapeutic blood plasma levels of genistein over an extended period of time.

The genistein formulations described herein are suitable for oral and parenteral administration. Additionally, the formulations described herein potentially provide several advantages. For example, because they can be used to achieve therapeutic plasma concentrations of genistein using less amounts of drug substance and, in some embodiments, relatively fewer doses, the formulations described herein may reduce the costs of genistein treatments as well as any potential side effects that may be associated with relatively higher doses of the compound. Moreover, because the formulations described herein enable delivery of therapeutic amounts of genistein using relatively smaller administered amounts of formulated drug, they may ease patient compliance and expand the contexts in which administration of genistein may be utilized.

The formulations described herein also exhibit desirable stability characteristics, are scalable for commercial production and, in specific embodiments, may increase the circulating half-life of genistein after administration.

Methods of treating subjects at risk for or suffering from various diseases and disorders suitable for treatment using genistein are also described herein.

I. Definitions

It must be noted that as used herein and in the appended claims, the singular forms "an," and "the" include plural reference unless the context clearly dictates otherwise, Thus, for example, reference to "a buffer" includes a plurality of such buffers, reference to "the buffer" is a reference to one or more buffers and equivalents thereof known to those skilled in the art, and so forth.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "nanoparticulate" refers to material exhibiting a volume diameter, as measured using laser light diffraction, wherein the D (0.50) of the material is 0.5 μm or less and no particles measure greater then 2 μm. Particle size analysis using laser light diffraction is a technique based on light being scattered through various angles which are directly related to the size of the particles. By measuring the angles of light scattered by the particles being analyzed and the intensity of this scattered light, a particle size distribution can be calculated. Techniques for use in analyzing particle size in the context of the present disclosure can be referred to as static light scattering, Rayleigh light scattering, low angle light scattering (LALS), multiple angle light scattering (MALS) Fraunhofer diffraction, or Mie Scattering. Measurement of particle size distributions using Mie Scattering allows for the determination of particle size distributions through the direction measurement of mass.

Two theoretical applications to the analysis of particle size by laser light diffraction are based on assumptions about the properties of the particles. Fraunhofer theory considers the following: particles are spherical, non-porous and opaque; particle diameters are greater than the wavelength of the laser light used in the analysis; and particles are distant enough from each other not to interfere in the diffraction of light, exhibit random motion, and diffract light with the same efficiency regardless of size and shape. Mie theory considers the differences in refractive index between the particles and the suspending medium, which allows the measurement technique to account for particles in the size range below the wavelength of the laser light used in the analysis. The relative amounts of different size particles are determined by measuring the intensity of light scattered at different angles. As the particles get close to or smaller than the wavelength of light, more of the light intensity is scattered to higher angles and back-scattered, Mie Scattering Theory accounts for this different behavior. In order to make particle size measurements, the light intensity pattern is measured over the full angular range. When the particle size is larger than the wavelength of the incident light, the Mie equation reduces to the Fraunhofer equation. An array of detectors, including high-angle and back-scatter detectors, and multiple light sources of different wavelengths are typically employed to allow measurement of the full size range in one analysis. Equipment suited for use in analyzing particle size by laser light diffraction is commercially available and manufactured, for example, by Horiba Instruments, Irvine, Calif.

The term "volume diameter" as used herein refers to the size of a particle as measured using a laser diffraction particle size analyzer, operating in the Mie Scattering Theory diffraction mode, equipped with a suspension dispersion sample chamber (e.g., as available from Horiba Instruments, Irvine, Calif., USA). For purposes of the present description, volume diameter is given as a particle size distribution defined by one or more of D (0.10), D (0.50) and D (0.90). When referred to herein, the term D (0.10) indicates the volume frequency distribution of particles for which 10% of the sample is below the referenced size, the term D (0.50) indicates the volume frequency distribution of particles for which 50% of the sample is below the referenced size, and the term D (0.90) indicates the volume frequency distribution of particles for which 90% of the sample is below the referenced size.

The term "parenteral" as used herein refers to delivery of an active agent or formulation to a subject via any route or means other than oral administration. For example, for purposes of the present disclosure, parenteral formulations include formulations and systems for topical, transdermal, and buccal delivery. The term "parenteral" as contemplated herein further encompasses delivery via suppository and compositions suited to formulation as a suppository. For purposes of the present disclosure, the term "parenteral" additionally encompasses delivery via infusion or injection, such as, for example, intravenous injection, intravenous infusion, intravascular injection, subcutaneous injection, and intramuscular injection.

As used herein, "pharmaceutical composition" refers to a composition that includes genistein in combination with one or more pharmaceutically acceptable excipients or adjuvants and is suitable for oral or parenteral administration to a subject.

The term "radioprotective agent" refers to agents that protect cells or living organisms from the deleterious cellular effects that result from exposure to ionizing radiation. These deleterious cellular effects include damage to cellular DNA, such as DNA strand break, disruption in cellular function, cell death and/or carcinogenesis. More particularly, the hematopoietic system is a rapidly dividing system and is therefore centrally affected by exposure to high-dose whole body ionizing radiation. Bone marrow aplasia and the resultant leukopenia, erythropenia and thrombocytopenia predispose the animal or human to infection, hemorrhage and ultimately death. For purposes of the present disclosure, a radioprotective agent may be one that is administered prophylactically prior to potential radiation exposure, with such administration resulting in the prevention, reduction in severity, or slowing of the symptoms or effects of exposure to ionizing radiation, should such an exposure occur. Additionally, a radioprotective agent may be used as a treatment for radiation exposure, administered after exposure to ionizing radiation has occurred, with such administration resulting in mitigation (i.e., prevention, reduction in severity, slowing, halting, or reversal of symptoms or effects that are otherwise associated with exposure to a given dose of ionizing radiation).

A "subject" for purposes of this disclosure is an animal to which a formulation as described herein can be administered in order to achieve a therapeutic effect. In one embodiment, the subject is a human being.

"Therapeutically effective" refers to an amount of genistein or an amount of a formulation of genistein as described herein which achieves a therapeutic effect by inhibiting a disease or disorder in a patient or by prophylactically inhibiting or preventing the onset of a disease or disorder. A therapeutically effective amount may be an amount which relieves to some extent one or more symptoms of a disease or disorder in a patient; returns to normal either partially or completely one or more physiological or biochemical parameters associated with or causative of the disease or disorder; and/or reduces the likelihood of the onset of the disease of disorder.

II. Genistein Formulations

Genistein is one of several known isoflavones that are normally found in plants. The main sources of natural genistein are soybeans and other legumes. Genistein is commercially available and may be obtained in synthetic, purified form. Synthetic genistein is available, for example, as BONISTEIN from DSM Nutritional Products (DSM Nutritional Products, Inc. Parsippany, N.J.). Genistein's chemical name is 5,7-dihydroxy-3-(4-hydroxyphenyl)-chromen-4-one (IUPAC). Genistein's chemical structure is shown as:

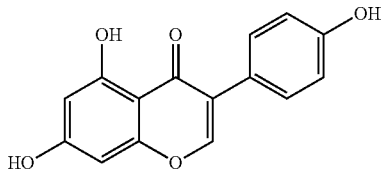 [SMILES: O=c1c(-c2ccc(O)cc2)coc2cc(O)cc(O)c12]

The genistein formulations described herein are suspension formulations that include nanoparticulate genistein suspended in a suspension medium formed of one or more carriers, excipients, and/or diluents. In particular embodiments, the formulations are provided as pharmaceutical compositions, and the carriers, excipients and/or diluents used in forming such compositions are selected from pharmaceutically acceptable materials. Pharmaceutically acceptable carriers, excipients and diluents suited for therapeutic use are well known in the pharmaceutical art, and are described, for example, in Remington's Pharmaceutical Sciences, Maack Publishing Co. (A.R. Gennaro (Ed.) 1985). In one such embodiment, the formulations as disclosed herein may include a suspension comprising nanoparticulate genistein suspended within a suspension medium including a water soluble polymer and a nonionic surfactant. The genistein used in the formulations described herein may be naturally derived or synthetically produced genistein. Pharmaceutical compositions of genistein as described herein can be formulated to be simultaneously suitable for both oral and parenteral administration. Though the formulations of genistein described herein are characterized as suspensions, in some embodiments, depending on the carriers, excipients and diluents included in the medium within which the nanoparticulate genistein is suspended, a measurable amount of genistein may also be dissolved within the suspension medium.

Nanoparticulate genistein suitable for use in the formulations disclosed herein may be prepared according to known methods for producing nano-sized particles. In one embodiment, natural or synthetic genistein material may be nanomilled according to milling techniques known in the art. In one embodiment, nanomilling may include wet bead milling utilizing an agitator bead mill in a horizontal grinding container for continuous dispersion and fine wet grinding. In another embodiment, using a bead mill such as a DYNO-mill (CB Mills, Gurnee, Ill.), the necessary energy for dispersion and grinding is transmitted to the grinding beads through agitator discs mounted on an agitator shaft.

In one embodiment, a nanoparticulate genistein composition as described herein is provided by introducing genistein suspended in a pharmaceutically acceptable suspension medium into a bead mill. In such an embodiment, the genistein suspension is fed into the bead mill and milled in a manner that results in a pharmaceutical genistein composition characterized by nanoparticulate genistein suspended within the pharmaceutically acceptable suspension medium. In one such embodiment, a genistein suspension formulation may be fed continuously through the bead mill until a suspension composition containing nanoparticulate genistein material of a defined particle size distribution is reached. For example, the genistein formulation may be nanomilled by recirculating the volume of the suspension through the bead mill, followed by one or more single passes through a bead mill to reach a pharmaceutical composition exhibiting the desired genistein particle size distribution. The particle size of the genistein material suspended within a pharmaceutical composition as described herein can be controlled by adjusting the parameters of the bead mill and the grinding conditions. For example, the particle size produced by nanomilling genistein or a genistein suspension formulation in a bead mill may be controlled by bead size, bead load/suspension weight ratio, suspension composition, agitation rate, and milling time.

Though nanomilling is generally referenced herein as a means for producing nanoparticulate material suitable for use in the formulations described herein, the nanoparticulate material can be produced other suitable techniques as well. For example, nanoparticulate genistein material as used herein can be produced using one or more known wet milling techniques, super-critical or compressed fluid techniques, hot or high-pressure homogenization, emulsification techniques, evaporative precipitation, antisolvent precipitation, microprecipitation, cryogenic techniques, complexation techniques, ultrasonication techniques, or solid dispersion techniques. Spray drying and lyophilization may be used post-processing to isolate nanoparticles resulting from an aqueous or solvent dispersion technique.

The genistein included in the formulations described herein is a nanoparticulate material as defined herein. In one embodiment, the compositions disclosed herein may comprise nanoparticulate genistein material exhibiting a D (0.50) of 0.2 μm or less. In on such embodiment, the nanoparticulate genistein material exhibits a D (0.50) of 0.2 μm or less and a D (0.90) of 0.5 μm or less. In yet another embodiment, the nanoparticulate genistein material exhibits a D (0.50) of 0.2 μm or less and a D (0.90) of 0.4 μm or less.

The nanoparticulate genistein material included in the formulations described herein is suspended within a suspension medium that includes one or more carriers, excipients and/or diluents. As described herein, in particular embodiments, such carriers, excipients and diluents are selected from pharmaceutically acceptable materials to facilitate preparation of pharmaceutical compositions that can be administered to a subject at risk for or suffering from a disease or disorder, such as, for example, a disease or disorder as described herein.

One or more nonionic surfactants may be included in the suspension medium to facilitate wetting and aid in preventing agglomeration of the nanoparticulate genistein drug substance. Nonionic surfactants suitable for use in the formulations described herein may be selected from, for example, polysorbates, poloxamers, polyoxyethylene castor oil derivatives (e.g., Cremophor EL, Cremophor RH60), bile salts, lecithin, 12-Hydroxystearic acid-polyethylene glycol copolymer (e.g., Solutol HS 15), and the like. In specific embodiments, the formulations described herein include a nonionic surfactant selected from polysorbate 80 (Tween 80), polysorbate 20 (Tween 20), Poloxamer 188, and combinations thereof. In one embodiment, the total nonionic surfactant content ranges from about 0.01% to about 10% by weight (w/w). In another embodiment, the total nonionic surfactant content ranges from about 0.1% to about 10% (w/w). In certain such embodiments, the total amount of nonionic surfactant is selected from about 0.2% to about 5% (w/w), about 0.2% to about 1% (w/w), about 0.2% to about 1% (w/w), about 0.2% to about 0.6% (w/w), and about 0.2% to about 0.8% (w/w).

The suspension formulations described herein may include one or more water soluble polymers, which may serve, for example, to enhance the viscosity of the suspension or to stabilize nanoparticulate genistein against particle agglomeration or potential deleterious effects from other formulation components. Water soluble polymers are pharmaceutically acceptable polymers that can be dissolved or dispersed in water. Suitable water soluble polymers for use in the formulations described herein may be selected from, for example, vegetable gums, such as alginates, pectin, guar gum, and xanthan gum, modified starches, polyvinyl pyrrolidone (PVP), hypromellose (HPMC), methylcellulose, and other cellulose derivatives, such as sodium carboxymethylcellulose, hydroxypropylcellulose, and the like. In certain embodiments, the formulations described herein may include a poloxamer, such as Poloxamer 188, as a water soluble polymer. Poloxamer 188 is both a polymer and surfactant. In other embodiments, the formulations described herein may include Povidone K17 as a water soluble polymer. Where one or more water soluble polymers are included in the suspension formulations described herein, in specific embodiments, the total water soluble polymer content ranges from about 0.5% to about 15% (w/w). For example, in certain such embodiments, the total water soluble polymer content ranges from about 1% to about 10% (w/w). In other such embodiments, the total water soluble polymer content may be selected from about 5% to about 15% (w/w), about 10% to about 15% (w/w), and 12% to about 15% (w/w), about 1% to about 8% (w/w), and about 1% to about 5% (w/w).

In particular embodiments, the suspension medium included in the suspension formulation includes a combination of one or more nonionic surfactants with one or more water soluble polymers. Where that is the case, the nonionic surfactant constituent and water soluble polymer constituent can be selected from the materials already described herein, including combinations of such materials. Moreover, where the suspension medium includes a combination of nonionic surfactant and water soluble polymer, the total nonionic surfactant and total water soluble polymer included in the suspension formulation can be selected from those amounts already detailed. For example, where the suspension medium includes a combination of nonionic surfactant and water soluble polymer, the total nonionic surfactant content may be selected from about 0.01% to about 10% (w/w), about 0.1% to about 10% (w/w), about 0.2% to about 5% (w/w), about 0.2% to about 1% (w/w), about 0.2% to about 1% (w/w), about 0.2% to about 0.6% (w/w), and about 0.2% to about 0.8% (w/w), and the total water soluble polymer content may be selected from about 0.5% to about 15% (w/w), about 1% to about 10% (w/w), about 5% to about 15% (w/w), about 10% to about 15% (w/w), about 12% to about 15% (w/w), about 1% to about 8% (w/w), and about 1% to about 5% (w/w). In one such embodiment, the nonionic surfactant constituent may be present in an amount ranging from about 0.1% to about 1% (w/w) and the water soluble polymer constituent may be present in an amount ranging from about 1% to about 15% (w/w), In another such embodiment, the nonionic surfactant constituent may be present in an amount ranging from about 0.2% to about 1% (w/w) and the water soluble polymer constituent may be present in an amount ranging from about 5% to about 15% (w/w). In specific embodiments of the suspension formulations where the suspension medium includes both a nonionic surfactant and a water soluble polymer, the nonionic surfactant may be selected from a polysorbate, such as polysorbate 80 (Tween 80) and polysorbate 20 (Tween 20), the water soluble polymer may be selected from a poloxamer, such as Poloxamer 188, and a PVP, such as Povidone K17, with the nonionic surfactant and water soluble polymer being included in the formulation at any of the relative amounts detailed herein.

The suspension medium included in the suspension formulations according to the present description may also include a carrier. For example, carriers suitable for use in the formulations described herein include pharmaceutically acceptable aqueous carriers such as, for example, sterile water, physiologically buffered saline Hank's solution, Ringer's solution, and any other suitable aqueous carrier. The suspension formulations described herein can utilize buffers such as, for example, one or more of a citrate buffer, phosphate buffer, TRIS buffer, and a borate buffer to achieve a desired pH and osmolality, Far example, the typical pH range for formulating injectable pharmaceutical products is from about 2 to about 12. In some embodiments, the pH of the formulation may fall in a range that more closely approximates physiologic pH. For example, in certain embodiments, the suspension formulations described herein are formulated to exhibit a pH selected from a range of from about 4 to about 8 and a range of from about 5 to about 7.

The suspension formulations described herein can also include one or more diluents. Suitable diluents may be selected from, for example, pharmaceutically acceptable buffers, solvents and surfactants.

Suspension formulations prepared as described herein are suited to providing high concentration genistein formulations (i.e., formulations containing genistein in amounts of about 250 mg/mL or greater). Though genistein exhibits low to virtually no solubility in several pharmaceutically acceptable solvents, the nanoparticulate suspension formulations described herein can incorporate genistein up to and over 300 mg/ml. In specific embodiments, genistein formulations as described herein may incorporate genistein in amounts ranging from about 250 mg/mL to about 500 mg/mL. In certain such embodiments, the amount of genistein included in a suspension formulation as described herein may be selected from about 200 mg/ml to about 400 mg/ml, from about 250 mg/ml to about 350 mg/ml, and from about 275 mg/ml and about 325 mg/ml.

The relative amount of genistein included in the suspension formulations described herein may be varied, as desired, to achieve a formulation having a desired total content of genistein. For example, the suspension formulations as described herein may include up to about 85% (w/w) genistein. In certain such embodiments, the relative amount of genistein is selected from up to about 75% (w/w), up to about 65% (w/w), and up to about 50% (w/w). Alternatively, embodiments of the suspension formulations described herein may include an amount of genistein selected from a range of about 40% to about 75% (w/w), a range of about 40% to about 65% (w/w), a range of about 40% to about 50% (w/w), a range of about 50% to about 75% (w/w), and a range of about 50% to about 65% (w/w).

The inventors have also found that suspension compositions prepared according to the present description can increase bioavailability of genistein relative to solution formulations. In particular, as is illustrated in the experimental examples that follow, suspension formulations prepared as described herein exhibited significantly improved relative bioavailability when compared to solution formulations prepared using, for example, pharmaceutically acceptable PEG solvent. Such a result runs counter to what would be generally expected. For example, in certain embodiments, relative to a solution formulation of genistein or formulations of genistein incorporating larger sized genistein material, a suspension formulation as described herein provides an increase in peak total genistein serum concentrations of up to 300%. In particular such embodiments, the increase in peak total genistein serum concentration ranges from about 50% to about 300%, In other such embodiments, the increase in peak total genistein serum concentration is selected from about 50% or greater, about 75% or greater, about 100% or greater, and about 200% or greater.

The combination of high drug loading and significantly increased relative bioavailability provided by formulations described herein present several advantages. The significant jump in drug loading by the genistein suspension formulations described herein facilitates administration of therapeutically effective amounts of genistein to subjects in need thereof using much less formulated drug substance, which, in turn, can increase patient compliance and facilitate manufacture of a genistein drug product that is much better suited to administration of genistein in therapeutic contexts requiring delivery of relatively high doses of genistein. Moreover, the increase in bioavailability afforded by the genistein suspension formulations described herein provides the added benefit of reducing the amount of genistein that must be delivered to a subject in order to achieve and maintain therapeutic genistein blood plasma levels. Therefore, the formulations described herein offer a significant reduction in the relative amount of administered genistein required to achieve and maintain a therapeutic benefit, which can reduce the costs of genistein treatments, work to mitigate or avoid potential side effects that may be associated with relatively higher doses of the compound, and further decreases the amount of formulated drug substance required to achieve and maintain therapeutic efficacy.

Even further, the suspension formulations taught herein can be formulated such that that a single given formulation is suited to both oral and parenteral delivery. Where a suspension formulation as described herein is prepared for parenteral delivery it can be manufactured according to standard methods to provide a sterile composition deliverable via, for example, intravenous injection or infusion, intravascular injection, subcutaneous injection, or intramuscular injection. The suspension formulations described herein can be prepared to exhibit viscosities suited for the desired route of parenteral administration and can be manufactured and packaged in any manner suited to the desired application, including, for example, as a formulation deliverable via intravenous injection or infusion, intravascular injection, subcutaneous injection, or intramuscular injection. In certain embodiments, the formulations described herein may be included in pre-filled syringes prepared for administration of a given dose or range of doses of genistein.

Where prepared for oral administration, the formulations may be prepared in any suitable manner and using any suitable devices for oral administration of desired doses of genistein. For example, when the formulations described herein are prepared for oral delivery, they may be prepared as a liquid suspension that can be metered to deliver a desired dose or incorporated into capsules, such as gelatin or soft capsules, suited for delivery of liquid formulations. Alternatively, formulations as described herein prepared for oral administration can be loaded into prefilled sachets or premetered dosing cups. Genistein formulations prepared for oral administration may optionally include one or more pharmaceutically acceptable sweetening agents, preservatives, dyestuffs, flavorings, or any combination thereof.

III. Methods

The genistein suspension formulations described herein can be used to treat subjects suffering from or at risk for a disease or disorder treatable with genistein. Clinical trials, animal studies, cell-culture experiments, and epidemiological studies have provided evidence that genistein exerts various physiological effects. Examples of diseases and disorders amenable to treatment by genistein are described herein. However, the potential therapeutic applications of genistein are not limited to those described herein, and genistein formulations according to the present description can be used to treat a subject at risk for or suffering from any disease or disorder for which administration of genistein will be therapeutically effective.

As one example, genistein has displayed antitumor, antimetastatic and antiangiogenic (suppression of blood-vessel growth) properties in tissue culture and in vivo. Several epidemiological studies suggest that soybean consumption may contribute to lower incidence of breast, colon, prostate, thyroid, and head and neck cancers—an effect that is attributed to genistein and other isoflavones (Takimoto et al., Cancer Epidemiol Biomarkers Prev. 2003 Nov.; 12(11 Pt 1): 1213-21; Wei et at, J Nutr. 2003 Nov.; 133(11 Suppl 1): 3811S-3819S; Sakar, F. H. and Y. Li, Cancer Invest. 2003; 21(5): 744-57; Magee P. J. and I. R. Roland, Br J Nutr. 2004 Apr.; 91(4): 513-31; Park, O. J. and Y. J. Surh, Toxicol Lett. 2004 Apr. 15; 150(1): 43-56; Messina, M. J., Nutr Re. 2003 Apr.; 61(4): 117-31). Genistein has also been reported to inhibit non-Hodgkin's lymphoma, melanoma, lung cancers, and ovarian cancer (Wei et al. 2003; Mohammad et at, Mol Cancer Ther. 2003 Dec.; 2(12): 1361-8; Nicosia et at, Hematol Oncol Clin North Am. 2003 Aug.; 17(4): 927-43; Sun et at, Nutr Cancer. 2001; 39(1): 85-95). Tissue culture experiments suggest that genistein's cancer-fighting effects occur at dosages that are hard to attain from food alone, unless one eats very large amounts of soy products. Reliable genistein dosing therefore requires the use of concentrated supplements (Magee and Roland 2004).

The genistein formulations may, therefore, be used in methods of inhibiting the onset, development or progression of certain cancers, such as cancers selected from breast, colon, prostate, thyroid, and head and neck cancers. In one such embodiment, a subject at risk for developing a breast, colon, prostate, thyroid, head or neck cancer is identified and a therapeutically effective amount of a genistein formulation selected from any of those described herein is administered to the subject. The genistein formulations described herein may also be used in methods of treating cancer. In a particular embodiment, a patient at risk for or suffering from a cancer responsive to genistein treatment, such as for example, a cancer selected from non-Hodgkin's lymphoma, melanoma, lung cancers, and ovarian cancer is identified and a therapeutically effective amount of a genistein formulation selected from any of those described herein is administered to the subject.

The ability of genistein and related soy isoflavones to reduce post-menopausal bone-loss has also been shown in many studies. These substances prevent bone loss and promote bone formation, especially in the spine. Among the dosage regimens found to be effective are: 1 mg/day genistein+0.5 mg/day daidzein+42 mg/day other isoflavones (biochanin A and formononetin, in this case); 54 mg/day genistein; 57 mg/day isoflavones; 65 mg/day isoflavones; 90 mg/day isoflavones (Morabito et al. J Bone Miner Res. 2002 Oct.; 17(10); 1904-12; Cotter A. and K. D. Cashman, Nutr Rev. 2003 Oct.; 61(10): 346-51; Atkinson et at, Am J Clin Nutr. 2004 Feb.; 79(2): 326-33; Setchell K. D. and E. Lydeking-Olsen, Am J Clin Nutr 2003 Sep.; 78(3 Suppl); 593S-609S; Clifton-Bligh et al., Menopause. 2001 Jul.-Aug.; 8(4): 259-65; Fitzpatrick, L. A., 2003 Mar. 14; 44 Supl 1: S21-9). Therefore, methods for reducing post-menopausal bone-loss are also provided herein. In one embodiment, such a method includes identifying a subject at risk for or suffering from post-menopausal bone loss and administering to the subject a therapeutically effective amount of a genistein formulation selected from any of those described herein. Alternatively, methods for promoting bone formation are also provided. In one such embodiment, a method for promoting bone formation, such as in the spine, includes identifying a subject at risk for or suffering from loss of bone mass and administering to the subject a therapeutically effective amount of a genistein formulation selected from any of those described herein.

Genistein has also been suggested for use in treating cystic fibrosis. The main clinical symptoms of cystic fibrosis are chronic obstructive lung disease, which is responsible for most of the morbidity and mortality associated with cystic fibrosis, and pancreatic insufficiency. Cystic fibrosis (CF) is caused by a mutation in the cystic fibrosis transmembrane conductance regulator (CFTR), a plasma membrane protein. CFTR functions as a chloride channel, and about 1000 mutations of the gene coding for CFTR are currently known. The most common of these known mutations results in a deletion of a phenylalanine at position 508 of the CFTR protein. This mutation is referred to as Delta508 and is present in the majority of patients suffering from cystic fibrosis. The Delta508 mutation results in an aberrant CFTR that is not transported to the plasma membrane, but is instead degraded in the ubiquitin-proteasome pathway. One approach for developing a treatment for cystic fibrosis is to inhibit the breakdown of DeltaF508-CFTR by interfering with the chaperone proteins involved in the folding of CFTR. Genistein has been shown in in-vitro systems to inhibit the breakdown of DeltaF508-CFTR through interference the relevant chaperone proteins. In addition, it has been shown that it is possible to stimulate CFTR or its mutated forms, when present in the plasma membrane, using genistein (Roomans, G. M., Am J Respir Med. 2003; 2(5): 413-31).

The genistein formulations described herein may be used in treating cystic fibrosis. In an embodiment of such a method, a subject at risk for or suffering from cystic fibrosis is identified and a therapeutically effective amount of a genistein formulation selected from any of those described herein is administered to the subject. In a particular embodiment, a subject at risk for or suffering from cystic fibrosis associated with DeltaF508-CFTR is identified and a therapeutically effective amount of a genistein formulation selected from any of those described herein is administered to the subject. In each embodiment of a method for treating cystic fibrosis described herein, the therapeutically effective amount of genistein formulation administered to the subject is sufficient to accomplish one or more of the following: inhibit the breakdown of DeltaF508-CFTR; inhibit or prevent the onset of cystic fibrosis or one or more symptoms associated with cystic fibrosis; mitigate or reduce the severity of one or more symptoms associated with cystic fibrosis; delay the progression of cystic fibrosis or the worsening of one or more symptoms associated with cystic fibrosis.

Genistein appears to increase the rate at which fats are metabolized by the body, and to decrease the rate at which they are deposited in the tissues (Goodman-Gruen, D. and D. Kritz-Silverstein, Menopause. 2003 Sep.-Oct.; 10(5): 427-32). Moreover, in clinical studies of humans and animals, the consumption of genistein and daidzein resulted in loss of body fat, lower fasting insulin concentrations, lower LDL and higher HDL cholesterol, and improved insulin responses to blood sugar. Cholesterol benefits were seen at dosages of 42 mg/day of genistein plus 27 mg/day of daidzein (Bhathena, S. J. and M. T. Velasquez, Am J Clin Nutr. 2002 Dec.; 76(6): 1191-201; Urban et al., J Urol. 2001 Jan.; 165(1): 294-300). In addition to lowering LDL and raising HDL (mentioned above), genistein prevents the oxidation of LDL, a process thought to contribute to arterial plaques (Young, S. G. and S. Parthasarathy, West J Med. 1994 Feb.; 160(2): 153-54). The genistein formulations described herein can be used in methods for lowering LDL and/or raising HDL in subjects in need thereof. In one such embodiment, a subject at risk for or suffering from a high circulating level of LDL is identified and a therapeutically effective amount of a genistein formulation selected from any of those described herein is administered to the subject, wherein the therapeutically effective amount of genistein formulation is sufficient to lower the LDL levels or prevent or delay an increase in circulating LDL levels in the subject. In another embodiment, a subject that could benefit from an increase in circulating levels HDL is identified and a therapeutically effective amount of a genistein formulation selected from any of those described herein is administered to the subject, wherein the therapeutically effective amount of genistein formulation is sufficient to increase circulating HDL levels or prevent or delay decrease in circulating HDL levels in the subject.

Genistein is also a radioprotective agent. For example, genistein has been reported to increase hematopoiesis and survival in irradiated mice (Zhou, 2005; Land Auer, 2001, 2003 & 2005). The mechanism of action for this radioprotective effect may potentially involve several of genistein's known effects including inhibition of protein tyrosine kinases (PTKs) and PTK-triggered apoptosis, inhibition of topoisomerase II, inhibition of phosphatidylinositol turnover and the second messenger system, both agonist and antagonist estrogenic effects, reduction of stress gene expression through inactivation of Y/CCA-AT binding factor, increased antioxidant activity, apoptosis, cell cycle arrest and differentiation, improved immune defenses and/or increased AKT kinase levels. The beneficial effects of genistein may also be due, in part, to its antioxidant properties, reducing free radicals and stabilizing the cell membrane structure. Further, genistein may also have a role in protecting stem cells and/or stimulating proliferation.

Genistein administered prior to, during, and/or after exposure to radiation, may be used to eliminate or reduce the severity of deleterious cellular effects caused by exposure to ionizing radiation resulting from, for example, from a nuclear explosion, a spill of radioactive material, close proximity to radioactive material, cancer radiation therapy, diagnostic tests that utilize radiation, and the like. Genistein can be used for the treatment and prevention of Acute Radiation Syndrome (ARS) (sometimes known as radiation toxicity or radiation sickness). ARS is an acute illness caused by irradiation of a substantial portion of the body by a high dose of penetrating radiation (i.e., greater than 0.7 Gray (Gy) or 70 rads, with mild symptoms possible at doses as low as 0.3 Gy or 30 rads) over a very short period of time (usually a matter of minutes). It is thought that the major cause of ARS is depletion of immature parenchymal stem cells in specific tissues.

Methods for treating radiation exposure are, therefore provided herein. In each embodiment, a subject at risk of or that has suffered from exposure to radiation is identified and a therapeutically effective amount of a genistein formulation selected from any of those described herein is administered to the subject. In specific embodiments, the method of treating radiation exposure is a method for preventing ARS, wherein a subject at risk of ARS is identified and a therapeutically effective amount of a genistein formulation as described herein is administered to the subject before the subject is exposed to radiation. In other embodiments, the method of treating radiation exposure is a method for treating ARS, wherein a subject suffering from ARS is identified and a therapeutically effective amount of a genistein formulation as described herein is administered to the subject after the subject has suffered exposure to radiation. In yet other embodiments, a subject at risk of radiation exposure is identified, a therapeutically effective amount of a genistein formulation as described herein is administered to the subject prior to exposure to radiation, and, in the event the subject suffers from radiation exposure, administration of therapeutically effective amounts of genistein is continued after the radiation exposure occurs.

In additional embodiments, subjects at risk for or having suffered from a radiation exposure resulting from an event selected from cancer radiation therapy or a diagnostic test utilizing radiation are identified, and the subjects are administered a therapeutically effective amount of the genistein formulation. In one such embodiment, the genistein formulation is administered to the subject prior to radiation exposure in order to prevent or reduce the severity of the deleterious effects of such exposure. In another such embodiment, the genistein formulation is administered to the subject after radiation exposure in order to mitigate, reverse or reduce the severity of the deleterious effects of such exposure. In still another embodiment, the methods of treating radiation exposure resulting from an event selected from cancer radiation therapy or a diagnostic test utilizing radiation in a subject may include administering a genistein formulation as described herein both before and after radiation exposure.

In each of the embodiments of the methods described herein, the therapeutically effective amount of genistein formulation may be administered orally or parenterally. In specific embodiments, where the genistein formulation is administered parenterally, it may be administered, for example, via intravenous injection or infusion, subcutaneous injection, intravascular injection, or intramuscular injection. Where the formulation is administered orally, the formulation may be prepared in any manner suitable for oral administration, such as is described herein. The dose and dosing regimen most appropriate for a given embodiment of the therapeutic methods described herein may depend upon, for example, the subject being treated, the nature of the disease or disorder, as well as the severity of any symptoms suffered. Using formulations prepared as described herein, one of skill in the art will be able to identify the appropriate dose and dosing regimen useful for achieving therapeutic efficacy in each of the methods described herein. The genistein formulations described herein may be administered, for example, as a single dose, a regular daily dose, a two-times daily dose, a three-times daily dose, or according to another desired dosing schedule.

The total daily dose of genistein delivered using a formulation or method described herein may depend on the desired condition to be treated or the desired therapeutic effect. In specific embodiments, a therapeutically effective amount of a genistein formulation according to the present description may be an amount sufficient to deliver a dose of genistein ranging from about 50 mg/day to about 10,000 mg/day. In certain such embodiments, the amount of genistein formulation administered to the subject is sufficient to deliver a dose of genistein selected from about 50 mg/day to about 9,000 mg/day, about 50 mg/day to about 8,000 mg/day, about 50 mg/day to about 2,000 mg/day, about 100 mg/day to about 9,000 mg/day, about 100 mg/day to about 5,000 mg/day, about 100 mg/day to about 4,000 mg/day, and about 100 mg/day to about 2,000 mg/day.

EXAMPLES

Example 1—Solubility of Genistein

Calculated pka's for genistein range from 7-9, with the predicted solubility increasing above pH 7 in accordance with the lowest pKa. The calculated properties were used to design the appropriate pH range for the pH-solubility profile of genistein in several acceptable cosolvents, which was established to be pH 6-9. Solubility of genistein was increased at higher pH, however degradation was observed at pH 9, Table 1 shows the solubility results of genistein in selected pharmaceutically acceptable cosolvents,

TABLE 1

| Vehicle | Solubility at 25° C. (mg/mL) |
|---|---|
| Propylene Glycol | 6.2 |
| Polyethylene Glycol 300 (PEG300) | 110.5 |
| Polyethylene Glycol 400 (PEG400) | 115.1 |
| Ethanol | 25.0 |
| Dimethyl acetamide (DMA) | 141.3 |
| N-methyl pyrrolidone (NMP) | 238 |
| Citrate buffer pH 6 | Not detected |
| Phosphate buffer pH 7 | Not detected |
| TRIS buffer pH 8 | Not detected |
| Borate buffer pH 9, 3 days | Not detected |
| Borate buffer pH 9, 7 days | 0.043 |
| Borate buffer pH 9, 14 days | 0.005 |

The solubility of genistein in water is not detectable at pH 6-7, which implies the solubility is less than 0.02 mg/mL or ~0.00002 g/g $H_2O$ (lowest concentration), Based on the pH-solubility and solubility in cosolvents, it was determined that PEG400 would be the cosolvent to achieve highest solubility. Since parenteral formulations preferably have a maximum of 50% organic component, the addition of Ethanol (EtOH), Nmethylpyrrolidone (NMP) and a surfactant were considered, since these would be expected to enhance absorption from the injection site. Ethanol has the added benefit of reducing viscosity. Polysorbate 80 (Tween 80) was considered as a surfactant due to its use in approved parenteral dosage forms at levels as high as 12% (FDA Inactive Ingredients Guide), although a more common range is 0.1-1%. Solubility was further evaluated in two aqueous/organic mixtures with concentrations acceptable for a parenteral dosage form. Additionally, cyclodextrin formulations were evaluated. Solubility testing results for genistein are given in Table 2.

TABLE 2

| Vehicle | Solubility of GENISTEIN at 25° C. (mg/mL) |
|---|---|
| 10% Polysorbate 80/40% PEG400/50% 25 mM Phosphate Buffered Saline (pH 7) | 11 |
| 10% Polysorbate 80/10% EtOH/40% PEG400/40% 25 mM Phosphate Buffered Saline (pH 7) | 12 |
| 10% Polysorbate 80/10% NMP/40% PEG400/40% 25 mM Phosphate Buffered Saline (pH 7) | 19 |
| 30% Hydroxypropyl-β-cyclodextrin | 6 |
| 30% Sulfobutylether-β-cyclodextrin | 8 |

Example 2—Nanoparticulate Genistein Composition

None of the previously evaluated genistein formulations achieved the desired level of drug loading. In an effort to achieve higher drug loading, a sterile injectable suspension was prepared according to the present description. The formulation included nanoparticulate genistein that had been nanomilled with a vehicle solution of 5% Povidone K17 (w/w), 0.2% Polysorbate 80 (w/w), in 50 mM phosphate buffered saline (61 mM sodium chloride). The quantitative composition of the formulation is listed in Table 3.

TABLE 3

| Component | Amount | Amount per 1 L |
|---|---|---|
| Genistein | 300 mg/mL | 300 g |
| Polysorbate 80 | 2 mg/mL | 2 g |
| Povidone K17 | 40 mg/mL | 50 g |
| 50 mM Sodium Phosphate/61 mM Sodium Chloride | 0.948 mg/mL | 948 g |

The function of each component and excipient listed in Table 1 is as follows: 1) Polysorbate 80 is included as a surfactant to enable wetting and aid in preventing agglomeration of suspended genistein drug substance, 2) Povidone K17 is included as a viscosity enhancer to aid in stabilizing the genistein drug substance suspension, and 3) Sodium Phosphate Buffer, Sodium Chloride is included as the diluent and to achieve physiological osmolality and maintain pH for parenteral administration of the composition.

The composition of 50 mM Sodium Phosphate Buffer/61 mM Sodium Chloride solution is as shown in Table 4.

TABLE 4

| Component | Amount per 1 L |
|---|---|
| $NaH_2PO_4 \cdot H_2O$ | 6.9 g |
| NaCl | 3.56 g |
| NaOH | (pH adjust) |
| HCl | (pH adjust) |

Example 3—Second Nanoparticulate Genistein Composition

A second nanoparticulate genistein formulation as described herein was prepared. The nanomilled genistein was achieved using wet bead milling, utilizing an agitator bead mill in a horizontal grinding container for continuous dispersion and fine wet grinding in a closed system A DYNO®-Mill Type Multi Lab agitator bead mill was used to prepare the nanoparticulate genistein, wherein the necessary energy for dispersion and grinding was transmitted to the grinding beads via the agitator discs mounted on the agitator shaft. Material was continuously fed into the mill via a product pump. The gap setting of the dynamic gap separator, the diameter of the beads, and length of the milling period were used to determine the particle size distribution. The product was fed continuously through the mill until a defined particle size distribution was reached. Although the DYNO®-Mill Type Multi Lab agitator bead mill was utilized in this work, other high energy, wet bead milling process equipment may be utilized.

Two formulations were tested that incorporated either Polysorbate 80 or Poloxamer 188 as a wetting agent to maintain a stable particle size distribution. Povidone (Polyvinyl pyrrolidone (PVP)) K17 was used at the 5% level in the formulations as a viscosity enhancer as well as a stabilizer against particle agglomeration. The quantitative composition of the formulation is given in Table 5.

TABLE 5

| Component | Reference to Quality Standard | Amount (mg/mL) |
|---|---|---|
| Genistein | SP-001 | 300 |
| Polysorbate 80 | USP | 2 |
| Povidone K17 | USP | 50 |
| Sterile Water for Injection | USP | QS to 1 mL |

The formulation may also include the replacement of the sterile water with injection with a phosphate-buffered saline for pH control and osmolality (e.g., as provided in the formulation described in Example 2).

The formulations exhibited an excellent, reproducible and stable particle size distribution profile, with d(0.5) of less than 0.2 μm. Optical microscopy confirmed a uniform particle size in the suspension, Powder X-Ray diffraction (XRD) was performed to examine physical, crystalline changes to the genistein material as a result of the milling process or as a result of a formulation incompatibility. Analyses performed indicate that there was no change in crystal form post-milling for genistein drug substance and milled suspensions containing 0.2% (w/w) polysorbate 80 with 5% (w/w) povidone K17, and 0.2% (w/w) poloxamer 188 with 5% (w/w) povidone K17.

The nanomilled genistein suspension comprised of nanoparticulate genistein (300 mg/mL) containing 0.2% (w/w) Polysorbate 80 with 5% (w/w) Povidone K17 was placed on stability at 5° C., 30° C. at 65% RH, and 40° C. at 75% RH. The suspensions were stored in 5 mL serum vials and 20 mm PTFE-faced butyl rubber stoppers. No impurities were observed after 7 months and there was no significant change in the particle size distribution.

Example 4—In-Vivo Comparison of Genistein Suspension Formulation with Genistein Solution Formulation This experiment evaluated a nanoparticulate formulation of genistein according to the present description and compared it to administration of genistein in a PEG 400 solution formulation. The genistein suspension formulation included nanomilled genistein in 50 nM phosphate buffered saline with 0.2% (w/w) Polysorbate 80 and 5% (w/w) PVP K17. The suspension formulation exhibited a pH of 6.96, and the nanoparticulate genistein incorporated into the suspension formulation exhibited a D (0.50) of 0.126 μm and a D (0.90) of 0.253 μm. The formulations were administered via subcutaneous injection ("SC") 24 hr prior to irradiation. A separate vehicle and genistein group was included for each formulation. The study was conducted at two radiation doses, either, 8.75 Gy or 9.0 Gy.

Male CD2F1 mice were exposed to bilateral whole-body irradiation at a dose of 8.75 Gy or 9.0 Gy at 0.6 Gy/min. Thirty-day survival was the endpoint for this study. The different experimental groups evaluated in this study are detailed in Table 6.

TABLE 6

Experimental Groups:

| Group | Route | Time of SC. | Gy | N | 30 Day Survival (%) |
|---|---|---|---|---|---|
| At 8.75 Gy: | | | | | |
| 1.) Vehicle, PEG-400 | SC | −24 Hr pre-rad | 8.75 | 16 | 38% |
| 2.) Genistein (PEG-400) | SC | −24 Hr pre-rad | 8.75 | 16 | 81% |
| 3.) Vehicle (Nano)) | SC | −24 Hr pre-rad | 8.75 | 16 | 25% |
| 4.) Genistein (Nano) | SC | −24 Hr pre-rad | 8.75 | 16 | 100%* |
| At 9.0 Gy: | | | | | |
| 1.) Vehicle, PEG-400 | SC | −24 Hr pre-rad | 9.0 | 16 | 38% |
| 2.) Genistein (PEG-400) | SC | −24 Hr pre-rad | 9.0 | 16 | 81%* |
| 3.) Vehicle (Nano) | SC | −24 Hr pre-rad | 9.0 | 16 | 19% |
| 4.) Genistein (Nano) | SC | −24 Hr pre-rad | 9.0 | 16 | 88%* |

As shown in Table 6 and FIG. 1, the thirty-day survival rates in groups receiving solution formulation of genistein (Genistein (PEG-400)) and suspension formulation of genistein (Genistein (NANO)) at 8.75 Gy were 81% and 100%, respectively. Survival rates of the control groups (Vehicle (PEG-400) and Vehicle (Nano)) were 38% and 25%, respectively. At 9.0 Gy, 30-day survival rates of the Genistein (PEG-400) group and the Genistein (NANO) group were 81% end 88% respectively. The survival rates of the control groups (Vehicle (PEG-400) and Vehicle (Nano)) were 38% and 19%, respectively. Every group that received genistein 24 hr pre-irradiation were significantly (p<0.05) different from their respective control group.

Example 5—In-Vivo Comparison Genistein Suspension Formulation Administered Parenteral and Genistein Suspension Formulation and Genistein Solution Formulation Given Orally This experiment evaluated the effect of a genistein nanoparticulate suspension formulation (Genistein-IS) prepared as described in Example 4 given via intramuscular injection ("IM") compared to the effect of a PEG 400 solution formulation and the Genistein IS suspension formulation given orally. The different formulations were administered twice daily for 6 days prior to irradiation. A positive control was also included which was Genistein-IS administered IM 24 hours prior to irradiation. A separate vehicle and genistein group was included for each group. The study was conducted at one radiation dose, 9.25 Gy. Male CD2F1 mice were exposed to bilateral whole-body irradiation at a dose of 9.25 Gy at 0.6 Gy/min Thirty-day survival was the endpoint for this study.

TABLE 7

Experimental Groups:

| Group | Route | Time of SC | Gy | N | 30 Day Survival (%) |
|---|---|---|---|---|---|
| 1) Vehicle, IS | IM | 24 Hr pre-rad | 9.25 | 20 | 10% |
| 2) Genistein IS | IM | 24 Hr pre-rad | 9.25 | 20 | 85%* |
| 3) Vehicle, IS | PO | BID for 6 days pre-rad | 9.25 | 20 | 15% |
| 4) Genistein IS | PO | BID for 6 days pre-rad | 9.25 | 20 | 85% |
| 5) Vehicle, PEG 400 | PO | BID for 6 days pre-rad | 9.25 | 20 | 0% |
| 6) Genistein/PEG 400 | PO | BID for 6 days pre-rad | 9.25 | 20 | 80%* |

*$p < 0.05$ two-tailed Fisher Exact Test (vehicle vs. genistein)
BID = twice daily dosing
IS = Injectable Suspension As shown in Table 7, the thirty-day survival rates of orally administered Genistein/PEG 400 and Genistein-IS at 9.25 Gy were 80% and 85%, respectively. Survival rates of the control groups (vehicle only administration) were 0% and 15%, respectively. The positive control group, Genistein IS administered IM 24 hours prior to irradiation, had a survival percentage of 85% vs. 10% for the vehicle.

Every group that received genistein either IM or orally were significantly (p<0.05) different from their respective negative control group. There was not, however, a significant difference in survival between genistein/PEG-400, and the Genistein IS formulation.

Example 6—Radio Protection Time Course Study with Vehicle Injection Suspension and Genistein Nano Particulate Injection Suspension Subcutaneously Administered 24 Hr, 18 Hr, 12 Hr, or 6 Hr Before 9.0 Gy $^{60}$Co Radiation Previous experiments showed statistically significant radioprotective results when a nanoparticulate genistein injectable suspension prepared according to the present description (Genistein-IS) was administered 24 hr before irradiation in a saline based vehicle. This time course study was performed to determine whether there was a time-dependent effect on radioprotective efficacy with SC administered Genistein-IS. The time dependent effects of Genistein-IS were compared to a placebo formulation (Vehicle-IS). The Genistein-IS formulation was prepared as described in Example 4.

Male CD2F1 mice were used in this experiment. All groups received a single 200 mg/kg SC administration at 24 hr, 18 hr, 12 hr, or 6 hr before irradiation. SC injections were administered in the nape of the neck using a 25 G needle in an injection volume of 0.1 ml via a 1 ml tuberculin syringe. All mice were exposed to bilateral whole-body irradiation at a dose of 9.0 Gy at 0.6 Gy/min. Thirty-day survival was the endpoint for this study.

TABLE 8

Experimental Groups:

| Group | Route | Time of Dose | Gy | N | 30-Day Survival (%) |
|---|---|---|---|---|---|
| 1.) Vehicle-IS | SC | 24 Hr pre-rad | 9.0 | 16 | 44% |
| 2) Genistein-IS | SC | 24 Hr pre-rad | 9.0 | 16 | 88%* |
| 3.) Vehicle-IS | SC | 18 Hr pre-rad | 9.0 | 16 | 13% |
| 4.) Genistein-IS | SC | 18 Hr pre-rad | 9.0 | 16 | 69%* |
| 5.) Vehicle-IS | SC | 12 Hr pre-rad | 9.0 | 16 | 44% |
| 6.) Genistein-IS | SC | 12 Hr pre-rad | 9.0 | 16 | 81% |
| 7.) Vehicle-IS | SC | 6 Hr pre-rad | 9.0 | 16 | 38% |
| 8.) Genistein-IS | SC | 6 Hr pre-rad | 9.0 | 16 | 63% |

*p < 0.05 two-tailed Fisher Exact Test (vehicle vs. genistein)

Figure 2:
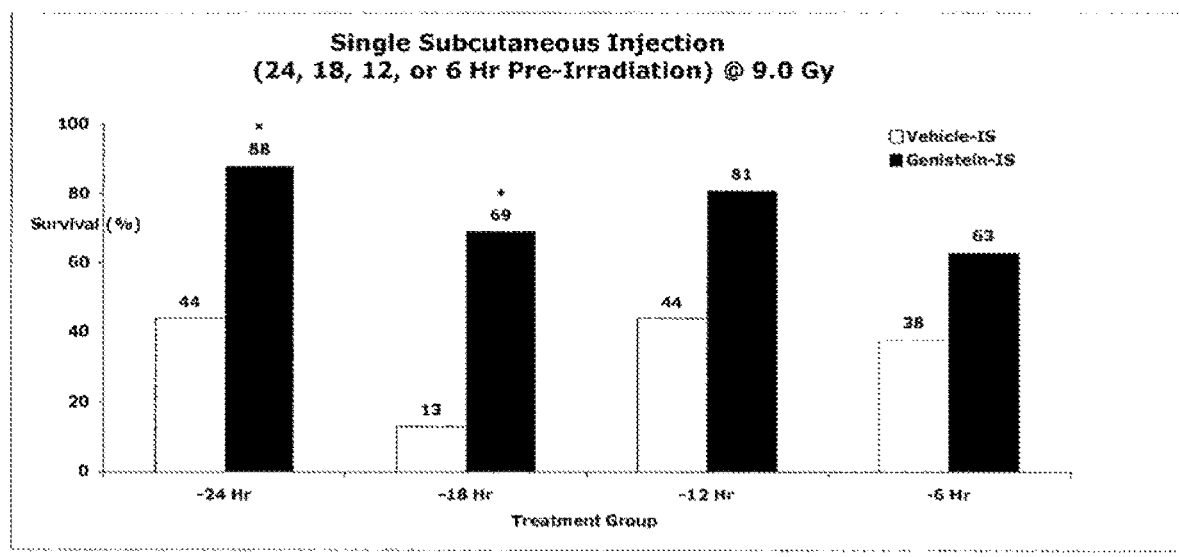
FIG. 2 shows the thirty-day survival rates of mice after subcutaneous administration of a genistein suspension formulation as described herein at 24, 18, 12, or 6 hr pre-irradiation.

The results shown in Table 8 and FIG. 2 demonstrate that a single SC administration of Genistein-IS administered at 24, 18, 12, or 6 hr pre-irradiation resulted in 30-day survival rates of 88%, 69%, 81%, and 63%, respectively. The survival rates for the Vehicle-IS groups at the corresponding time points were 44%, 13%, 44%, and 38%, respectively. Genistein-IS resulted in significant radioprotection when injected either 24 or 18 hr before irradiation (p<0.05).

Example 7—Effect of Subcutaneous Vs. Intramuscular Injection of Nanoparticulate Genistein Formulation on Radioprotective Efficacy when Administered 24 hr Before 9.25 Gy$^{60}$Co Radiation The purpose of this experiment was to compare the radioprotective efficacy of a nanoparticulate genistein suspension formulation prepared as described herein (Genistein-IS) delivered to provide a genistein dose of 200 mg/kg when administered SC or IM. The Genistein-IS formulation was prepared as described in Example 4. Male CD2F1 mice were used in this experiment. Groups were given a single SC or IM injection of an injectable placebo suspension (Vehicle-IS) or Genistein-IS (200 mg/kg) 24 hr before irradiation. Also included in this experiment were groups that received a solution formulation of genistein in PEG 400 (Genistein) delivered to provide a genistein dose of 200 mg/kg or placebo PEG 400 formulation (PEG 400) administered SC 24 hr before irradiation.

All vehicle and Genistein-IS groups received a single 200 mg/kg SC or IM injection at 24 hr before irradiation. SC injections were administered in the nape of the neck using a 25 G needle in an injection volume of 0.1 ml via a 1 ml tuberculin syringe. Mice were administered Vehicle-IS or Genistein-IS by IM injection into the quadriceps muscle using a 25 G needle attached to a Hamilton syringe. The injection volume was 50 µl.

Mice were exposed to bilateral whole-body irradiation at a dose of 9.25 Gy at 0.6 Gy/min. Thirty-day survival was the endpoint for this study.

TABLE 9

Experimental Groups:

| Group | Route | Time of Dose | Gy | N | 30-Day Survival (%) |
|---|---|---|---|---|---|
| 1.) PEG 400 | SC | 24 Hr pre-rad | 9.25 | 20 | 15% |
| 2.) Genistein | SC | 24 Hr pre-rad | 9.25 | 20 | 75%* |
| 3.) Vehicle IS | SC | 24 Hr pre-rad | 9.26 | 20 | 30% |
| 4.) Genistein IS | SC | 24 Hr pre-rad | 9.25 | 20 | 85%* |
| 5.) Vehicle IS | IM | 24 Hr pre-rad | 9.25 | 20 | 15% |
| 6.) Genistein IS | IM | 24 Hr pre-rad | 9.25 | 20 | 75%* |

*p < 0.05 two-tailed Fisher Exact Test (vehicle vs. genistein)

Figure 3:
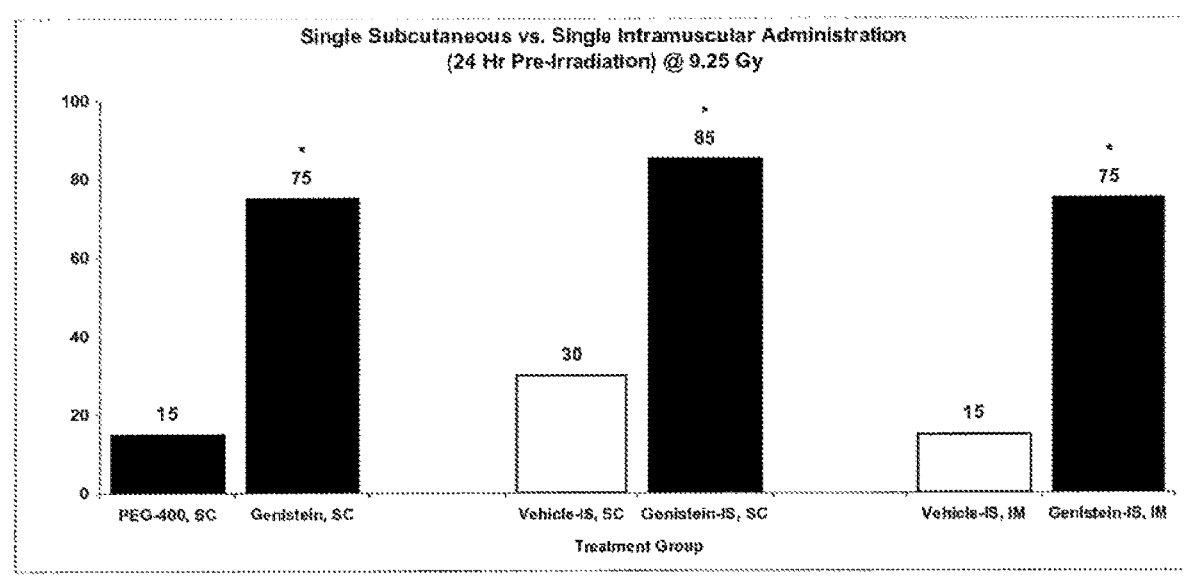
FIG. 3 shows the thirty-day survival rates of mice after subcutaneous and intramuscular administration of a genistein suspension formulation as described herein.

Survival rates for vehicle-PEG 400 and genistein PEG 400 administered SC were 15% and 75%, respectively. This resulted in statistically significant radioprotection by genistein over PEG 400 vehicle (p<0.05) (shown in Table 9 and FIG. 3).

When Vehicle-IS or Genistein-IS was administered SC, 30-day survival rates were 30% and 85%, respectively. For IM administration, survival rates for Vehicle-IS and Genistein-IS, were 15% and 75%, respectively. For both SC and IM routes, genistein provided significant protection over vehicle (p<0.05) (shown in Table 9 and FIG. 3).

These results demonstrate that nanoparticulate genistein formulations prepared according to the present description provide similar levels of radioprotection when administered by either the SC or IM route.

Example 8—Pharmacokinetics in Mice Following Intravenous or Intramuscular Injection of $^{14}$C-Genistein As shown in the results of Table 10, male CD1 mice were administered a single IM dose (Group 2, nominal 200 mg/kg) or a single IV bolus dose (Group 3, nominal 50 mg/kg) of $^{14}$C-Genistein. The genistein formulation used was a suspension formulation that includes genistein suspended in sterile water with 0.2% (w/w) Polysorbate 80 and 5% (w/w) PVP K17. The genistein material used in the suspension formulation exhibited a D (0.50) of 0.136 µm and a D(0.90) of 0.310 µm. Following dosing, the content and concentration of radioactivity in blood, plasma, excreta and carcass, and the non-compartmental pharmacokinetics of total radioactivity in whole blood and plasma were determined, Following dose administration, the extent and severity of any clinical signs was assessed. The dose level of 200 mg/kg (IM) and 50 mg/kg (IV) were well tolerated and therefore chosen for the main study.

The concentration of radioactivity in both dose formulations was measured pre and post dose by liquid scintillation spectroscopy and was similar on both occasions. The radiochemical stability of the test article in both dose formulations was assessed prior to and following the administration of the dose. The mean radiochemical stability of the test article in the dose formulation samples from the intramuscular dose formulation (Group 2) were 98.5% and 98.2%, respectively. The mean radiochemical stability values for pre and post dose samples from the intravenous dose formulation (Group 3) were 98.3% and 98.5%, respectively. Therefore, the $^{14}$C-Genistein in both formulations was considered to have been radiochemically stable throughout the dosing period. No treatment-related clinical signs were observed in any of the main study male mice following a single IM dose of $^{14}$C-Genistein (200 mg/kg) or a single IV dose of $^{14}$C-Genistein (50 mg/kg).

Whole-blood samples were collected and plasma was obtained by centrifugation. The concentration of radioactivity in whole-blood and plasma was measured by liquid scintillation spectroscopy. Pharmacokinetic parameters were calculated from the composite concentration vs. time profiles and are presented in Table 10.

TABLE 10

| Pharma-cokinetic Parameter | Units | Group 2 (IM) | | Group 3 (IV) | |
|---|---|---|---|---|---|
| | | Blood | Plasma | Blood | Plasma |
| $t_{max}$ | h | 0.50 | 0.50 | 0 | 0 |
| $C_{max}$ | µg eq/mL | 33.3 | 63.1 | 60.1 | 108 |
| $t_{last}$ | h | 168 | 168 | 168 | 168 |
| $AUC_{0-tlast}$ | µg eq · h/mL | 222 | 375 | 99.7 | 116 |
| $R^2$ | — | 0.977 | 0.943 | 0.850 | 0.999 |
| $k_{el}$ | $h^{-1}$ | 0.0242 | 0.0145 | 0.0118 | 0.0307 |
| $t_{1/2}$ | h | 28.7 | 47.8 | 58.5 | 22.6 |
| $AUC_{0-inf}$ | µg eq · h/mL | 223 | 387 | 112 | 116 |
| Extrapolation | % | 0.663 | 3.18 | 11.4 | 0.191 |
| $V_d$ | mL/kg | NA | NA | 37554 | 14042 |
| CL | mL/h/kg | NA | NA | 445 | 431 |
| Bioavailibility | % | 49.7 | 83.5 | NA | NA |

For Group 2, the highest mean concentration of radioactivity in plasma and whole blood was observed at 30 minutes post dose (first time point analyzed), suggesting a rapid absorption from the IM dose. Blood to plasma ratios of less than 1 suggested that dose-related material was not particularly associated with the blood cells at any time post dose. Exposure of plasma to dose-related material was greater than that of whole blood, as measured by $AUC_{0-inf}$, and the rate of clearance was slower (as measured by $t_{1/2}$). The systemic exposure ($AUC_{0-inf}$) following the IM administration was relatively good with an estimation of relative bioavailability of total radioactivity of 49.7% and 83.5% for blood and plasma, respectively.

For Group 3, the highest mean concentration of radiolabelled material in plasma and whole blood was observed at 30 minutes post dose (the first time point analyzed). For the early time points (0 to 24 hours), concentrations in plasma were always higher than those in blood, as reflected by blood-to-plasma ratios of less than 1. This indicated that dose-related material was not particularly associated with the blood cells at these time points. After 24 hours, the concentrations of radioactivity in blood were always higher than those in plasma suggesting that the dose-related material was associated with the blood cells. Exposure of plasma to dose-related material was similar to whole blood, as measured by $AUC_{0-inf}$, but the rate of clearance was faster as measured by $t_{1/2}$.

The major route of excretion following an IM dose or an IV bolus dose was via urine, with a smaller percentage recovered in feces. The recoveries in excreta following the intramuscular and intravenous doses were very similar, at approximately 52.5% to 54.0% for urine and at approximately 31.3% to 35.5% for feces. For both dose routes, excretion was relatively rapid with the majority of the dose administered excreted within 24 hours. The proportion of the administered radiolabelled material recovered in feces suggested that biliary excretion of dose-related material had occurred following both dose routes. Excretion recovery was approximate 92% and 93% for Groups 2 and 3, respectively, indicating that excretion was essentially complete by 168 hours post dose. A small percentage of the administered radiolabelled material, for both routes, was found in the remaining carcass. Thus the overall mean mass balance of radioactivity was good, at approximately 93% to 94% of the administered dose for both Groups 2 and 3 animals.

In conclusion, male mice were administered an IM dose (200 mg/kg) or an IV bolus dose (50 mg/kg) of $^{14}$C-Genistein. Concentrations of radioactivity in whole blood, plasma, excreta and carcass were determined. The highest radioactivity concentrations were observed at 30 minutes post intramuscular or intravenous bolus dose, indicating rapid absorption from the intramuscular dose. The bioavailability of dose-related material following the intramuscular dose was good, at greater than 49%. Radioactivity was excreted rapidly and urine was the major route of excretion for both dose routes. The high level of radioactivity recovered in feces following the intramuscular or intravenous bolus dose suggested that biliary excretion had occurred. The total recovery of dose-related material following both dose routes was essentially complete by 168 hours post dose.

Example 9—Pharmacokinetics in Beagle Dogs Following Intravenous or Intramuscular Injection of $^{14}$C-Genistein Male Beagle dogs were administered a single IV bolus dose (Group 1, nominal 20 mg/kg) or a single IM dose (Group 2, nominal 20 mg/kg) of $_{14}$C-Genistein (results shown in Table 11). The Genistein suspension formulation used was prepared as described in Example 8, Following dosing, the content and concentration of radioactivity in blood, plasma and excreta, and the non-compartmental pharmacokinetics of total radioactivity in whole blood and plasma were determined. The concentration of radioactivity in both dose formulations was measured pre and post dose by liquid scintillation spectroscopy and was similar on both occasions. The radiochemical stability of the test article in both dose formulations was assessed prior to and following the administration of the dose. The mean stability values for pre and post dose samples from the intravenous dose formulation (Group 1) were 100% and 99.6%, respectively. The mean stability values for pre and post dose samples from the intramuscular dose formulation (Group 2) were 99.2% and 98.9%, respectively. Therefore, the $^{14}$C-Genistein in both formulations was considered to have been radiochemically stable throughout the dosing period.

Whole-blood samples were collected and plasma was obtained by centrifugation. The concentration of radioactivity in whole-blood and plasma was measured by liquid scintillation spectroscopy. Pharmacokinetic parameters were calculated from the concentration vs. time profiles and are presented in Table 11.

TABLE 11

| Pharma-cokinetic Parameter | Units | Group 1 (IV) | | Group 2 (IM) | |
|---|---|---|---|---|---|
| | | Blood | Plasma | Blood | Plasma |
| $t_{max}$ | h | 0 | 0 | 2 | 2 |
| $C_{max}$ | µg eq/mL | 40.4 | 94.4 | 5.39 | 10.9 |
| $t_{last}$ | h | 120 | 120 | 168 | 168 |
| $AUC_{0-tlast}$ | µg eq · h/mL | 117 | 201 | 108 | 193 |
| $k_{el}$ | $h^{-1}$ | 0.0130 | 0.0138 | $a$ | 0.0092 |
| $t_{1/2}$ | h | 55.7 | 227 | $a$ | 75.2 |
| $AUC_{0-inf}$ | µg eq · h/mL | 122 | 227 | $a$ | 228 |
| Extrapolation | % | 16.8 | 11.3 | $a$ | 15.1 |
| $V_Z$ | mL/kg | 13168 | 6511 | NA | NA |

TABLE 11-continued

| Pharma-cokinetic Parameter | Units | Group 1 (IV) | | Group 2 (IM) | |
|---|---|---|---|---|---|
| | | Blood | Plasma | Blood | Plasma |
| CL | mL/h/kg | 163 | 88.7 | NA | NA |
| Bio-availibility | % | NA | NA | 92.9 | 96.1 |

[a]extrapolation to $AUC_{0-inf}$ greater than 20%, therefore not reported. NA not applicable For Group 1 (IV bolus dose), the highest mean concentration of radiolabelled material in plasma and whole blood was observed at 15 minutes post dose (the first time point analyzed). Concentrations in plasma were always higher than those in blood, as reflected by blood to plasma ratios of less than 1. This indicated that dose-related material was not particularly associated with the blood cells at these time points. Exposure of plasma to dose-related material was greater than that of whole blood, as measured by $AUC_{0-inf}$, but the rate of clearance was similar as measured by $t_{1/2}$.

For Group 2 (IM dose), the highest mean concentration of radioactivity in plasma and whole blood was observed at 2 hours post dose, suggesting a relatively rapid absorption from the intramuscular dose. Blood to plasma ratios of less than 1 suggested that dose-related material was not particularly associated with the blood cells at any time post dose. Exposure of plasma to dose-related material was greater than that of whole blood, as measured by $AUC_{0-tlast}$. The rate of clearance (as measured by $t_{1/2}$) was generally slower than the one observed following the IV bolus dose. However, the systemic exposure ($AUC_{0-tlast}$) following the IM administration was good with an estimation of relative bioavailability of total radioactivity of 92.9% and 96.1% for blood and plasma, respectively.

The major route of excretion following an intravenous bolus dose or an IM dose was via feces, with a smaller percentage recovered in urine. The recoveries in excreta following the IV bolus and IM doses were very similar, at approximately 48.7 to 51.9% for feces and at approximately 32.0 to 33.6% for urine. For both dose routes, excretion was relatively rapid with the majority of the dose administered excreted within 48 hours. The proportion of the administered radiolabelled material recovered in feces suggested that biliary excretion of dose-related material had occurred following both dose routes. Excretion recovery by 168 hours post dose was approximately 87.9% and 85.8% for Groups 1 and 2, respectively. Thus, the overall mean excretion mass balance of radioactivity for both groups was good, at approximately 86-88% of the administered dose.

In conclusion, male dogs were administered an IV bolus dose (20 mg/kg) or an IM dose (20 mg/kg) of $^{14}$C-Genistein. Concentrations of radioactivity in whole blood, plasma and excreta were determined. Clinical signs were observed in both groups and were considered to be dose-related. The highest radioactivity concentrations in blood and plasma were observed at 15 minutes (intravenous dose) or 2 hours (intramuscular dose) post dose, indicating relatively rapid absorption from the IM dose. The bioavailability of dose-related material following the IM dose was good, at greater than 92%. Test article-related material was excreted rapidly and feces was the major route of excretion for both dose routes. The high level of radioactivity recovered in feces following the IV bolus or intramuscular dose suggested that biliary excretion had occurred. The excretion mass balance for both dose routes was considered good at greater than 85%.

Example 10—Oral Pharmacokinetic Comparison Study

An oral bioavailability comparison of genistein solution formulation in PEG 400 vs. a genistein nanosuspension prepare according to the present description was carried out. The genistein suspension formulation was prepared as described in Example 4. Considering the limited oral bioavailability of genistein in earlier preclinical and clinical work, this experiment was designed to compare a previously used genistein solution formulation prepared with PEG 400 as the vehicle with a genistein nanosuspension formulation prepared as described herein.

Ten groups of seven mice were prepared at each time point (70 mice) for each of the two formulations (total mice=140). A single dose of 400 mg/kg genistein was given by oral gavage and then blood was collected at 10 subsequent time points. Time points for blood collection were the following: 0, 0.5, 1, 2, 3, 4, 6, 8, 10 and 12 hours post administration.

Figure 4:
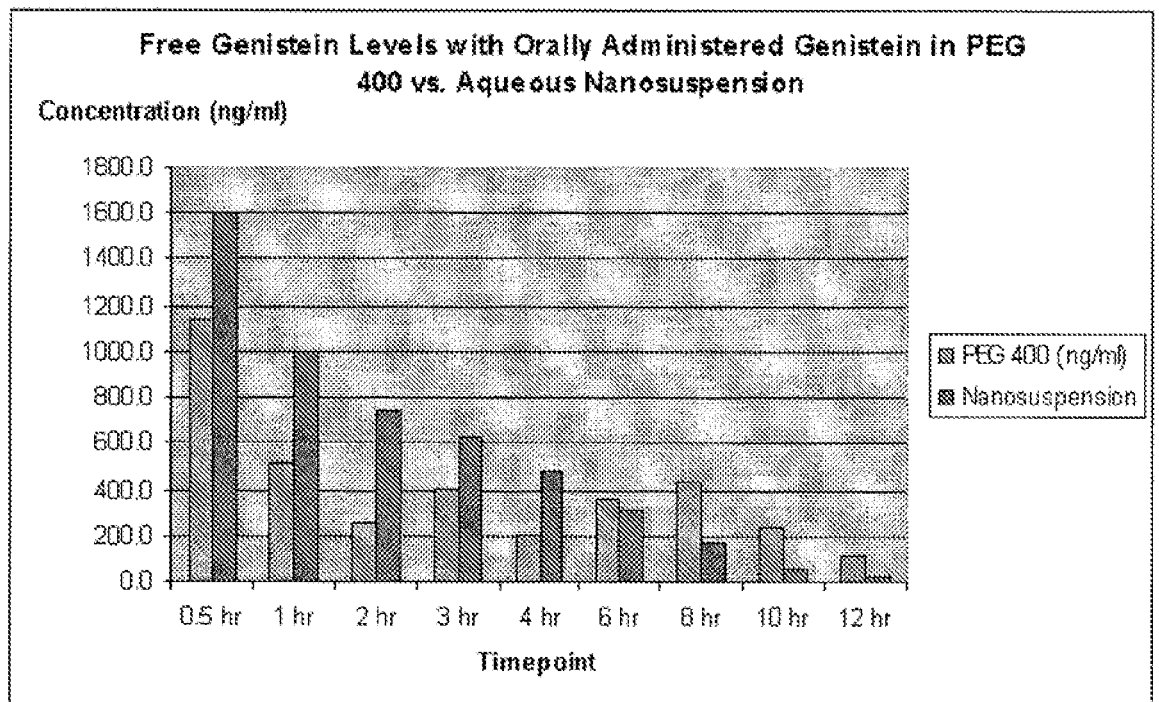
FIG. 4 shows the free genistein concentration achieved after oral administration of a genistein suspension formulation as described herein versus that achieved by a solution formulation of genistein.
Figure 5:
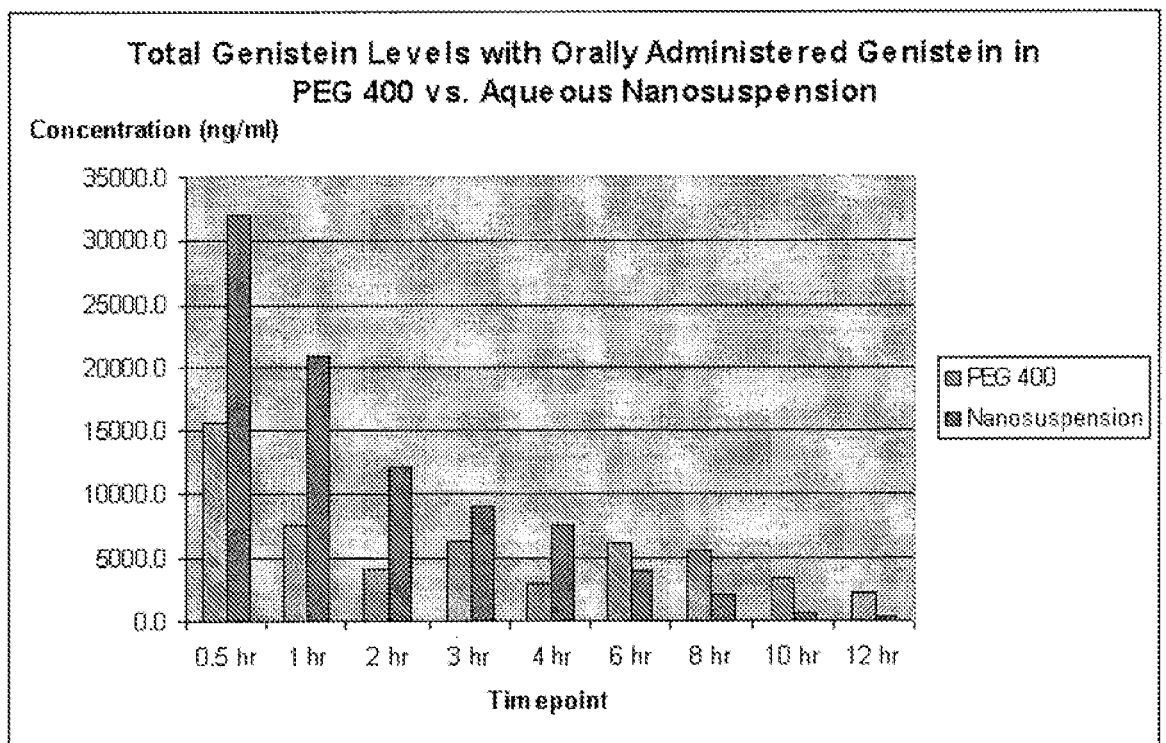
FIG. 5 shows the total genistein concentration achieved after oral administration of a genistein suspension formulation as described herein versus that achieved by a solution formulation of genistein.

The oral bioavailability with the nanoparticulate suspension was statistically significantly greater than that achieved in the PEG 400 solution formulation. Both free and total genistein levels were determined in each of the groups for every time point. The mean concentration of seven mice was determined for each time point and reported. At the time 0 time point, the free and total genistein concentration was below the limit of quantitation and not reported. For the mice receiving the nanoparticulate suspension, the free genistein concentrations were significantly greater at 1, 2, 4, 8, 10 and 12 hours when compared to the concentration achieved in the mice receiving the PEG 400 solution formulation. The total genistein concentrations were also significantly greater with the nanoparticulate suspension at 0.5, 1, 2, 4, 8, 10 and 12 hours when compared to the PEG 400 solution formulation. As noted in Table 12 and Table 13, and as shown in FIG. 4 and FIG. 5, the absorption and excretion curve for the nanoparticulate suspension is also much more predictable and less erratic than that achieved by the PEG 400 formulation for both the free and total genistein concentrations. Free genistein determinations after a single oral dose of 400 mg/kg for two different genistein formulations in mice.

TABLE 12

Mean Free Genistein Concentrations at Each Sampling Time point

| Time point | Free PEG 400 (ng/ml) | Free Nano-suspension (ng/ml) | Difference | Percent | p value |
|---|---|---|---|---|---|
| 0.5 hr | 1137.9 | 1598.6 | 460.7 | 40.5 | 0.062 |
| 1 hr | 514.0 | 999.7 | 485.7 | 94.5 | 0.006 |
| 2 hr | 255.1 | 746.4 | 491.3 | 192.6 | 0.000 |
| 3 hr | 403.1 | 634.6 | 231.4 | 57.4 | 0.079 |
| 4 hr | 207.6 | 484.3 | 276.7 | 133.2 | 0.002 |
| 6 hr | 361.9 | 313.6 | −48.4 | −13.4 | 0.791 |
| 8 hr | 436.3 | 172.3 | −264.0 | −60.5 | 0.023 |
| 10 hr | 239.0 | 59.0 | −180.0 | −75.3 | 0.000 |
| 12 hr | 113.7 | 28.3 | −85.4 | −75.1 | 0.034 |

TABLE 13

Mean Total Genistein Concentrations at Each Sampling Time point

| Time point | Total PEG 400 (ng/ml) | Total Nano-suspension (ng/ml) | Difference | Percent | p value |
|---|---|---|---|---|---|
| 0.5 hr | 15640.0 | 32114.3 | 16474.3 | 106.3 | 0.000 |
| 1 hr | 7711.4 | 20974.3 | 13262.9 | 172.0 | 0.002 |
| 2 hr | 4151.4 | 12050.0 | 7898.6 | 190.3 | 0.033 |
| 3 hr | 6251.4 | 9112.9 | 2861.5 | 45.8 | 0.136 |
| 4 hr | 2970.1 | 7692.9 | 4722.8 | 159.0 | 0.003 |
| 6 hr | 6215.1 | 4004.3 | −2210.8 | −35.6 | 0.257 |
| 8 hr | 5558.6 | 1982.9 | −3575.7 | −64.3 | 0.006 |
| 10 hr | 3480.0 | 755.4 | −2724.6 | −78.3 | 0.001 |
| 12 hr | 2205.0 | 380.3 | −1824.7 | −82.8 | 0.002 |

Example 11—Oral Bioavailability Comparison of Non-Nanoparticulate Genistein Suspension Formulation and a Nanoparticulate Genistein Formulation In a previous experiment we were able to demonstrate improved oral bioavailability with orally administered Genistein-IS suspension formulation in comparison with a formulation of genistein dissolved in PEG-400. This experiment compared the oral bioavailability of an aqueous genistein suspension formulation that included non-nanoparticulate genistein material with that provided by the Genistein-IS formulation prepared as described in Example 4. The non-nanoparticulate genistein suspension formulation was the same as the Genistein-IS formulation, except that the genistein material exhibited a volume average particle size of 8 μm, instead of the volume average particle size of 0.13 μm exhibited by the Genistein-IS suspension formulation.

Ten groups of seven mice were prepared at each timepoint (70 mice) for each of the two formulations (total mice=140). A single dose of 400 mg/kg was given by oral gavage and then blood was collected at 10 subsequent timepoints. Time points for blood collection were the following: 0, 0.5, 1, 2, 4, 6, 8, 10, 12 and 24 hours post administration.

Figure 6:
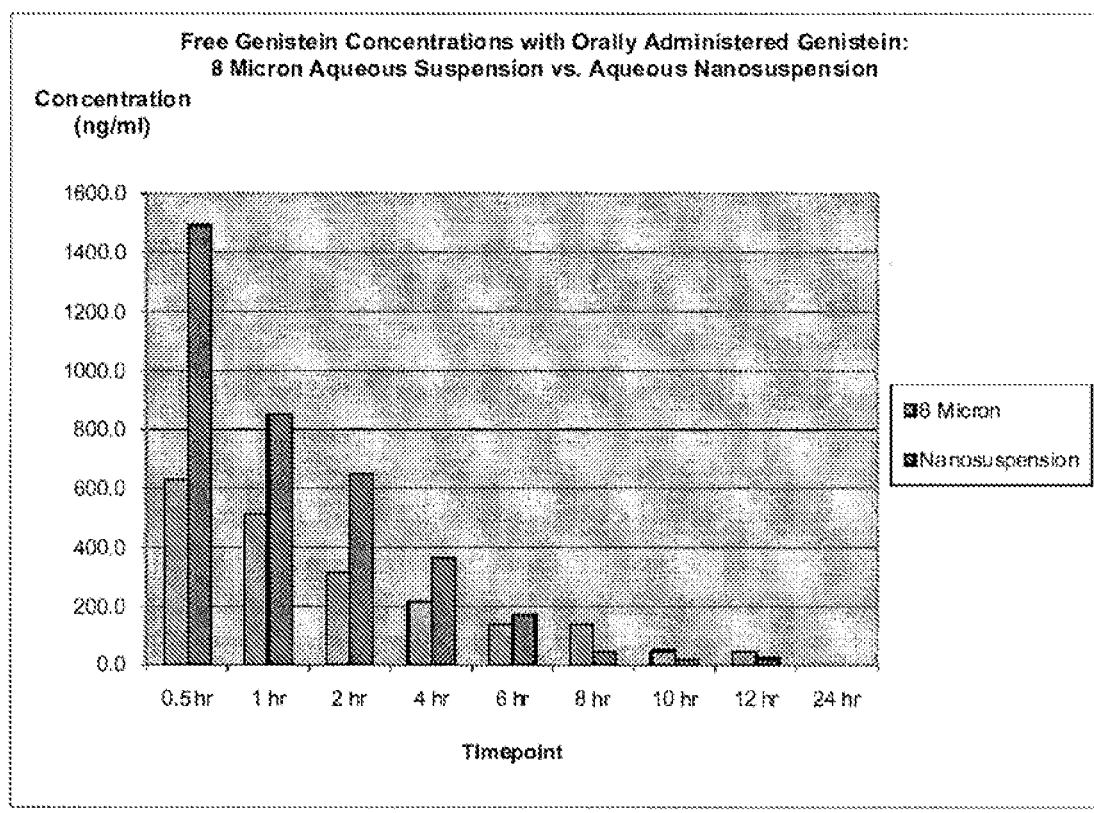
FIG. 6 shows the free genistein concentration achieved after oral administration of a genistein suspension formulation as described herein versus that achieved by a non-nanoparticulate suspension formulation of genistein.
Figure 7:
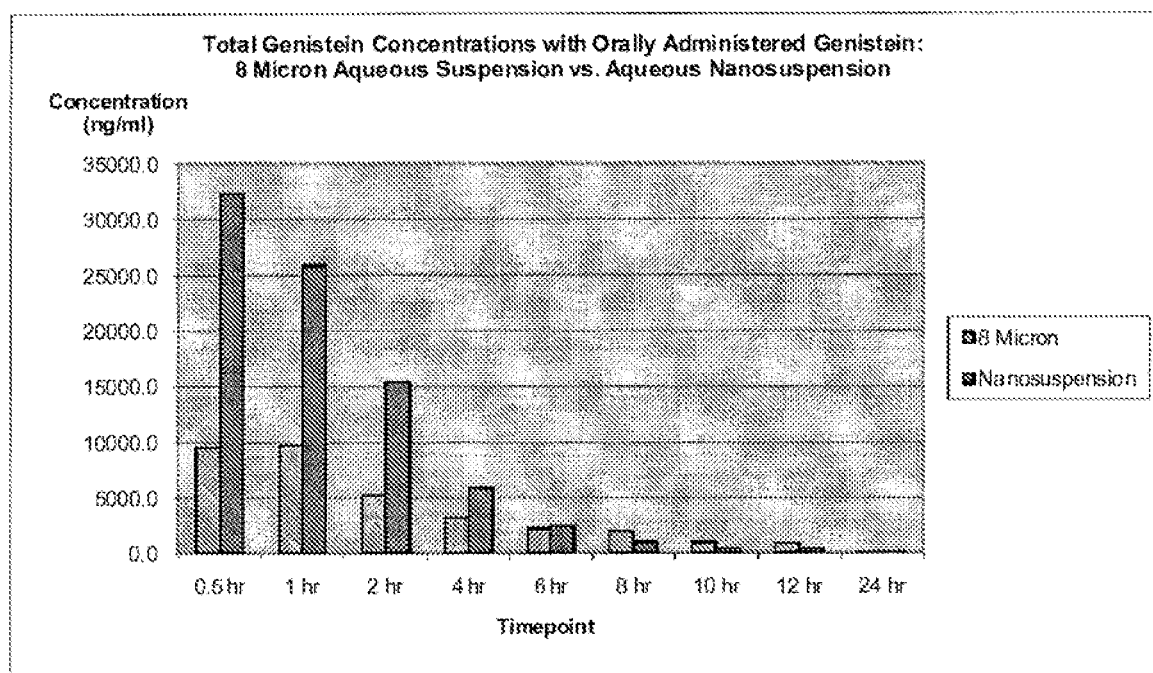
FIG. 7 shows the total genistein concentration achieved after oral administration of a genistein suspension formulation as described herein versus that achieved by a non-nanoparticulate suspension formulation of genistein.

Both free and total genistein levels were determined in each of the groups for every timepoint. The mean concentration of seven mice was determined for each timepoint and reported. At the time 0 timepoint, the free and total genistein concentration was below the limit of quantitation and not reported. For the Genistein-IS suspension formulation mice, the free genistein concentrations were significantly greater at 0.5, 1 & 2 hours when compared to those achieved by the non-nanoparticulate genistein formulation (See, Table 14). The total genistein concentrations were also significantly greater with the with the Genistein-IS suspension formulation at 0.5, 1 and 2 hours when compared to those achieved by the non-nanoparticulate genistein formulation (See, Table 15). As noted in FIG. 6 and FIG. 7, the absorption and excretion curve for the Genistein-IS suspension formulation is also much more predictable and less erratic than that achieved by the non-nanoparticulate genistein formulation for both the free and total genistein concentrations.

TABLE 14

Mean Free Genistein Concentrations at Each Sampling Timepoint

| Timepoint | Free Conc. 8 Micron (ng/ml) | Free Conc. Nano-suspension (ng/ml) | Difference | Percent | p value |
|---|---|---|---|---|---|
| 0.5 hr | 630.7 | 1494.0 | 863.3 | 136.9 | 0.000 |
| 1 hr | 512.1 | 853.4 | 341.3 | 66.6 | 0.003 |
| 2 hr | 314.4 | 652.6 | 338.1 | 107.5 | 0.003 |
| 4 hr | 214.3 | 367.4 | 153.1 | 71.5 | 0.055 |
| 6 hr | 136.3 | 168.0 | 31.7 | 23.2 | 0.460 |
| 8 hr | 140.1 | 45.8 | 94.3 | −67.3 | 0.006 |
| 10 hr | 60.3 | 21.6 | −28.6 | −57.0 | 0.284 |
| 12 hr | 47.3 | 23.0 | −23.3 | −49.4 | 0.195 |
| 24 hr | 0.0 | 0.0 | 0.0 | — | — |

TABLE 15

Mean Total Genistein Concentrations at Each Sampling Timepoint

| Timepoint | Total Conc. 8 Micron (ng/ml) | Total Conc. Nano-suspension (ng/ml) | Difference | Percent | p value |
|---|---|---|---|---|---|
| 0.5 hr | 9561.4 | 32385.7 | 22824.3 | 238.7 | 0.000 |
| 1 hr | 9762.9 | 25842.9 | 16080.0 | 164.7 | 0.000 |
| 2 hr | 5247.1 | 15357.1 | 10110.0 | 192.7 | 0.007 |
| 4 hr | 3230.0 | 5938.6 | 2708.6 | 83.9 | 0.055 |
| 6 hr | 2230.4 | 2423.1 | 192.7 | 8.6 | 0.802 |
| 8 hr | 1902.9 | 1007.1 | −895.7 | −47.1 | 0.070 |
| 10 hr | 1002.2 | 426.4 | −575.8 | −57.5 | 0.253 |
| 12 hr | 876.4 | 338.1 | −538.3 | −61.4 | 0.121 |
| 24 hr | 53.5 | 57.7 | 4.3 | 8.0 | 0.715 |

It will be obvious to those having skill in the art that many changes may be made to the details of the above-described embodiments without departing from the underlying principles of the invention. The scope of the present invention should, therefore, be determined only by the following claims.

The invention claimed is:

1. A method of preparing nanoparticulate genistein, comprising:
    combining genistein with a pharmaceutically acceptable suspension medium, the pharmaceutically acceptable suspension medium comprising an aqueous carrier:
    nanomilling the combined genistein and pharmaceutically acceptable suspension medium to form a nanosuspension containing nanoparticulate genistein exhibiting a particle size distribution characterized by a D (0.50) of 0.5 μm or less, wherein the nanoparticulate genistein is present in the nanosuspension at a concentration of between 250 mg/mL and 500 mg/mL; and
    subjecting the nanosuspension to one or more post-processing steps comprising spray drying the nanosuspension or lyophilizing the nanosuspension.

2. The method of claim 1, wherein the subjecting the nanosuspension to one or more post processing steps comprises spray drying the nanosuspension.

3. The method ref claim wherein the subjecting the nanosuspension to one or more post processing steps comprises lyophilizing of the nanosuspension.

4. The method of claim 1, wherein the nanoparticulate genistein exhibits a D (0.50) of 0.2 μm or less.

5. The method of claim 1, wherein the nanoparticulate genistein exhibits a D (0.50) of 0.2 μm or less and a D (0.90) of 0.5 μm or less.

6. The method of claim 1, wherein the nanoparticulate genistein exhibits a D(0.50) of 0.2 μm or less and a D (0.90) of 0.4 μm or less.

7. The method of claim 1, wherein the pharmaceutically acceptable suspension medium comprises a nonionic surfactant.

8. The method of claim 1, wherein the pharmaceutically acceptable suspension medium comprises a water soluble polymer.

9. The method of claim 1, wherein the pharmaceutically acceptable suspension medium comprises a nonionic surfactant and a water soluble polymer.

10. The method of claim 7, wherein the nonionic surfactant is a polysorbate.

11. The method of claim 7, wherein the nonionic surfactant is polysorbate 80.

12. The method of claim 8, wherein the water soluble polymer is a polyvinylpyrrolidone (PVP).

13. The method of claim 9, wherein the nonionic surfactant is polysorbate 80 and the water soluble polymer is PVP.

14. The method of claim 1, wherein the nanosuspension comprises a nonionic, surfactant and a water soluble polymer, wherein the nonionic surfactant is present in the nanosuspension in an amount ranging from about 0.01% to about 10% (wfw), and wherein the water soluble polymer is present in the nanosuspension in an amount ranging from about 0.5% to about 15% (w/w).

15. The method of claim 1, wherein the nanosuspension comprises a nonionic surfactant and a water soluble polymer, wherein the nonionic surfactant is present in the nanosuspension in an amount ranging from about 0.1% to about 1% (w/w), and wherein the water soluble polymer is present in the nanosuspension in an amount ranging from about 1% to about 15% (w/w).

16. The method of claim 1, the method further comprising adding a diluent to the nanosuspension prior to subjecting the nanosuspension to one or more post-processing steps.

17. The method of claim 16, wherein the subjecting the nanosuspension to one or more post processing steps comprises spray drying the nanosuspension.

18. The method of claim 16, wherein the subjecting the nanosuspension to one or more post processing steps comprises lyophilizing the nanosuspension.

19. An oral dosage form comprising:
nanoparticulate genistein prepared according to a method comprising:
combining genistein with a pharmaceutically acceptable suspension medium, the pharmaceutically acceptable suspension medium comprising an aqueous carrier;
nanomilling the combined genistein and pharmaceutically acceptable suspension medium to form a nanosuspension containing nanoparticulate genistein exhibiting a particle size distribution characterized by a D (0.50) of 0.5 μm or less, wherein the nanoparticulate genistein is present in the nanosuspension at a concentration of between 250 mg/mL and 500 mg/mL; and
subjecting the nanosuspension to one or more post-processing steps comprising spray drying the nanosuspension or lyophilizing the nanosuspension.

20. A method of preventing the onset of acute radiation syndrome in a subject at risk of exposure to radiation greater than 0,7 Gray or 70 rads through close proximity to radioactive material, the method comprising:
up to six days prior to the subject being exposed to said radiation, administering to the subject a therapeutically effective amount of an oral dosage form comprising nanoparticulate genistein prepared according to a method comprising (i) combining genistein with a pharmaceutically acceptable suspension medium, the pharmaceutically acceptable suspension medium comprising an aqueous carrier, (ii) nanomilling the combined genistein and pharmaceutically acceptable suspension medium to form a nanosuspension containing nanoparticulate genistein exhibiting a particle size distribution characterized by a D (0.50) of 0.5 μm or less, wherein the nanoparticulate genistein is present in the nanosuspension at a concentration of between 250 mg/mL and 500 mg/mL, (iii) and subjecting the nanosuspension to one or more post-processing steps comprising spray drying the nanosuspension or lyophilizing the nanosuspension.

* * * * *

UNITED STATES PATENT AND TRADEMARK OFFICE
CERTIFICATE OF CORRECTION

PATENT NO. : 10,729,674 B2
APPLICATION NO. : 16/026546
DATED : August 4, 2020
INVENTOR(S) : Edmund Joseph Elder, Jr. et al.

Page 1 of 1

It is certified that error appears in the above-identified patent and that said Letters Patent is hereby corrected as shown below:

In the Claims

Column 26, Line 46 in Claim 1, reads, "suspension medium comprising an aqueous carrier:" which should read, "suspension medium comprising an aqueous carrier;"

Column 26, Line 60 in Claim 3, reads, "3. The method ref claim wherein the subjecting the" which should read, "3. The method of claim 1, wherein the subjecting the"

Column 27, Line 23 in Claim 14, reads, "comprises a nonionic, surfactant and a water soluble poly-" which should read, "comprises a nonionic surfactant and a water soluble poly-"

Column 27, Line 26 in Claim 14, reads, "10% (wfw), and wherein the water soluble polymer is" which should read, "10% (w/w), and wherein the water soluble polymer is"

Column 28, Line 21 in Claim 20, reads, "than 0,7 Gray or 70 rads through close proximity to radio-" which should read, "than 0.7 Gray or 70 rads through close proximity to radio-"

Signed and Sealed this
Twenty-seventh Day of October, 2020

Andrei Iancu
*Director of the United States Patent and Trademark Office*